(12) United States Patent
Cochran et al.

(10) Patent No.: US 8,247,531 B2
(45) Date of Patent: Aug. 21, 2012

(54) MUTANT EPIDERMAL GROWTH FACTOR POLYPEPTIDES, NUCLEIC ACIDS, AND USES THEREFOR

(76) Inventors: Jennifer R. Cochran, Stanford, CA (US); K. Dane Wittrup, Chestnut Hill, MA (US)

(*) Notice: Subject to any disclaimer, the term of this patent is extended or adjusted under 35 U.S.C. 154(b) by 0 days.

(21) Appl. No.: 11/725,695

(22) Filed: Mar. 20, 2007

(65) Prior Publication Data
US 2008/0249008 A1    Oct. 9, 2008

Related U.S. Application Data

(60) Provisional application No. 60/784,274, filed on Mar. 20, 2006.

(51) Int. Cl.
*C07K 14/485* (2006.01)
*A61K 38/18* (2006.01)
(52) U.S. Cl. ......................................... 530/324; 514/9.6
(58) Field of Classification Search .................. None
See application file for complete search history.

(56) References Cited

U.S. PATENT DOCUMENTS
6,191,106 B1 * 2/2001 Mullenbach et al. .......... 514/7.6

FOREIGN PATENT DOCUMENTS
WO       2005/070960    *  8/2005

OTHER PUBLICATIONS

H.S. Shiah et al. "Pseudomonas Exotoxin A-Epidermal Grwoth Factor (EGF) Mutant Chimeric proteins as an Indicator for Identifying Amino acid Residues Important in EGF-Receptor Interaction", J. biol. Chem. 267(33): 24034-24040. (Nov. 1992).*

M.L.M. van de Poll et al. "A Single Amino Acid Exchange, Arg-45 to Ala, Generates an Epidermal Growth Factor (EGF) Mutant with High Affinity for the Chicken EGF Receptor", J. Biol. Chem. 270(38): 22337-22343. (Sep. 1995).*

Cochran, et al., "Improved mutants from directed evolution are biased to orthologous substitutions", *Protein Engineering, Design & Selection*, 2006, vol. 19, No. 6, pp. 245-253.

Coco, et al., "Growth factor engineering by degenerate homoduplex gene family recombination", *Nature Biotechnology*, 2002, vol. 20, pp. 1246-1250.

Mullenbach, et al., "Modification of a receptor-binding surface of epidermal growth factor (EGF): analogs with enhanced receptor affinity at low pH or at neutrality", *Protein Engineering*, 1998, vol. 11, pp. 473-480.

* cited by examiner

*Primary Examiner* — Rebecca E. Prouty
(74) *Attorney, Agent, or Firm* — Duane Morris LLP; Lee Crews

(57) ABSTRACT

The present invention is based, in part, on our discovery that EGF can be engineered to generate mutants that bind to the EGF receptor (EGFR) of a cell and that have a desirable effect on the activity of the cell. For example, the mutants can agonize the receptor (i.e., increase a biological activity of the receptor), or antagonize the receptor (i.e., decrease or inhibit a biological activity of the receptor). In turn, the rate at which the cell proliferates, for example, can be changed. Moreover, some of these mutants bind EGFR with a higher affinity than wild-type EGF exhibits. The affinity may increase by about, for example, 2-, 5-, 10-, 15-, 20-, 25-, 30-, 50-, or 100-fold relative to wild-type EGF.

11 Claims, 6 Drawing Sheets

FIG. 1

First Generation EGF Mutants:
Table I: EGF mutants produced by nucleotide analog mutagenesis

```
EGF wt      NSDSECPLSHDGYCLHDGVCMYIEALDKYACNCVVGYIGERCQYRDLKWWELR
Clone 27    NSDSGCPLSHDGYCLHDGVCMYIEALDKYACNCVVGYTGERCQYRDLRWWELR
Clone 28    NSDSECPLSHDGYCLHGGVCMYIKAVDRYACNCVVGYIGERCQYRDLTWWGPR
Clone 29    NSDSECPLSHDGYCLHDGVCVYIKTLDKYACNCVVGYAGERCQYRDLRWWELR
Clone 30    SSNSGCPLSHDGYCLHDGVCMYIEALDRYACNCVVGYAGERCQYRDLKWWELR
Clone 31    NSDSECPLSHDGYCLHDGACVYIEALDKYACNCVVGYVGERCQYRDLRWWGRR
Clone 33    NSGSECPLSHDGYCLHDGVCMYIEALDKYACNCVVGYIGERCQYRDLRWWELR
Clone 34    NSDSECPLSHDGYCLHDGACMYIEALDKYVCNCAVGYIGERCQYRDLRWWGPR
Clone 35    NGDSECPLSYDGYCLHDGVCMYIEALDKYACNCVVGYIGERCQYRDLKWWERR
Clone 43    NSDSECPLSHDGYCLHDGVCMYIEALDRYACNCVVGYIGERCQYRDLRWWELR
Clone 45    NSDSECPLSHNGYCLHDGVCMYIKALDKYACNCVAGYTGERCQYRDLRWWGLR
Clone 46    NSDSECPLSHDGYCLHDGVCMYIEALDKYACNCVVGYAGERCQYRDLRWWARR
Clone 51    NSGSKCPLSHDGYCLHDGVCMYIGALDRYACNCVVGYVGERCQYRDLRWWELR
```

FIG. 2A

Second Generation EGF Mutants:
Table II: EGF mutants produced through mutgenesis and DNA shuffling

```
EGF wt      NSDSECPLSHDGYCLHDGVCMYIEALDKYACNCVVGYIGERCQYRDLKWWELR
Clone  96   KSGPGCPPPYDGYCLQGGVCMYIGALDRYACNCVVGYIGERCQYRDLKWWEPR
Clone  97   NSDSECPLSHDGYCLHDGVCMYIKALDKYACNCVVGYTGERCQYRDLRWWGRR
Clone  99   YSDSECPLSHDGYCLHDGVCMYIEALDKYACNCVVGYAGERCQYRDLRWWELR
Clone 103   NSNSECPLSHDGYCLHDGVCRYIEALDRYACNCVVGYIGERCQYGDLRWWGRR
Clone 114   SRGSKCPPSHDGYCLQGGVCMYIEALDRYACNCVVGYAGERCQYRDLTWWGRR
Clone 115   NSDSGCPLSHSGYCLHDGVCMYIKALDRYACNCVVGYAGERCQYRDLRWWARR
Clone 116   SSGSERPPSHDGHCLHGGVCMYIEALDKYACSCAVGYTGERCQYRGLRWWGLR
Clone 130   NSDSECPPSHDGYCLQGGVCMYIEALDRYACNCVVGYIGERCQYRDLTWWEPR
Clone 131   TRGSECPLSHDGYCLHDGVCMYIGALDRYACNCVVGYTGERCQYRDLRWWARR
Clone 133   NSDFGCPLSYDGYCLHDGVCMYIKALDKYACNCVVGYAGERCQYRDLRWWGRR
Clone 134   SRGSKCPPSHDGYCLHDGVCMYIEALDRYACNCVVGYAGERCQYRDLRWWARR
```

FIG. 2B

Table III: EGF mutants produced through DNA shuffling, mutagenesis and oligo doping

```
EGF wt      NSDSECPLSHDGYCLHDGVCMYIEALDKYACNCVVGYIGERCQYRDLKWWELR
clone  91   SSGSECPSSHDGYCLHDGACMYIEALDRYACNCAVGYAGERCQYRDLRWWGRR
clone  92   SSNSECPPSHDGYCLHDGVCMYIEALDRYACNCVVGYAGERCQYRDLRWWARR
clone  93   NSYSECPLSHDGYCLHGGVCRYIEALDKYACNCVVGYSGERCQYRDLRWWGLR
clone  94   NSGSECPLSYDGYCLHGGVCMYIEALDRYACNCVVGYNGERCQYRDLKWWWLR
clone 100   NSNSECPLSHDGYCLNDGVCRYIEALDKYACNCVVGYVGERCQYRDLRRWELR
clone 101   NSGSECPLSYDGYCLNDGVCMYIGALDKYACNCVVGYTGERCQYQDLRWWKLR
clone 102   HSNSECPLSHDGYCLNDGVCMYIKALDTYACNCVVGYVGERCQYPDLKWWGLR
clone 107   NSYSECPLSYDGYCLNDGVCRYIEALDRYACNCVVGYIGERCQYRDLKWWWLR
clone 120   SRGSKCPPSHDGYCLNDGVCMYIEALDKYACNCVVGYLGERCQYRDLKWWYTR
clone 121   NSDPKCPLSHEGYCLNDGVCMYIGTLDRYACNCVVGYVGERCQYRDLKWLALR
clone 122   NSNSECPLSHDGYCLNDGVCKYIEALDRYACNCVVGYAGERCQYRDLRWWGLR
clone 123   NSYSECPPSYDGYCLHDGVCRYIEALDSYACNCVVGYAGERCQYRDLRWWGRR
clone 124   NSNSECPRSHDGYCLNDGVCMYIEALDRYACNCVVGYVGERCQYRDLRWWGLR
clone 129   SSGSECPLSHDGYCLNDGVCMYIEALDKYACNCVVGYVGERCQYRDLRWWARR
```

FIG. 3

EGF affinity mutants are biased towards homologous substitutions

```
Human       NSDSECPLSHDGYCLHDGVCMYIEALDKYACNCVVGYIGERCQYRDLKWWELR
Murine      NSYPGCPSSYDGYCLNGGVCMHIESLDSYTCNCVIGYSGDRCQTRDLRWWELR
Rat         NSNTGCPPSYDGYCLNGGVCMYVESVDRYVCNCVIGYIGERCQHRDLRWWKLR
Pig         NSYSECPPSHDGYCLHGGVCMYIEAVDSYACNCVFGYVGERCQHRDLKWWELR
Dog         NGYRECPSSYDGYCLYNGVCMYIEAVDRYACNCVFGYVGERCQHRDLK-WELR
Cat         NSYQECPPSYDGYCLYNGVCMYIEAVDRYACNCVFGYVGERCQHRDLK-WELR
Guinea Pig  QDAPGCPPSHDGYCLHGGVCMHIESLNTYACNCVIGYVGERCEHQDLD-WE--
Horse       NSYQECSQSYDGYCLHGGKCVYLVQVDTHACNCVVGYVGERCQHQDLR-----
Rabbit      SHFNQCPDSHTQFCFH-GTCRFLVQEDKPACVCHSGYVGARCEHADLLA----
```

FIG. 4

Previous EGF engineering studies

```
Human       NSDSECPLSHDGYCLHDGVCMYIEALDKYACNCVVGYIGERCQYRDLKWWELR
```

Site-Directed mutations:
G12Q, H16D, H16A, Y13W, Q43A, L15A (2)

Randomized mutations:
D46, R41 (16); Y13, L15, and H16 (17)

MUTANT EPIDERMAL GROWTH FACTOR POLYPEPTIDES, NUCLEIC ACIDS, AND USES THEREFOR

CROSS-REFERENCE TO RELATED APPLICATIONS

This application claims the benefit of priority of U.S. Ser. No. 60/784,274, filed Mar. 20, 2006, the contents of which is hereby incorporated by reference in its entirety.

FEDERALLY SPONSORED RESEARCH OR DEVELOPMENT

The work described herein was funded, in part, through grants from the National Institutes of Health (Grant No. BRP CA096504 awarded to K. Dane Wittrup, and Grant No. F32 CA94796-01 awarded to Jennifer R. Cochran). The United States government may, therefore, have certain rights in the invention.

TECHNICAL FIELD

This invention relates to epidermal growth factor polypeptides, including mutants of human epidermal growth factor, nucleic acids encoding the polypeptides, related therapeutics, and methods of use.

BACKGROUND

Epidermal growth factor (EGF) is a 6.2 kDa polypeptide that specifically binds to the epidermal growth factor receptor (EGFR). EGF contains 53 amino acids with three internal disulfide bridges. Binding of EGF to its receptor induces a conformational change and receptor aggregation (Greenfield, et al., *EMBO J.* 8:4115-4123, 1989; Yarden and Schlessinger, *Biochem.* 26:1443-1451, 1987). Receptor aggregation stimulates an intrinsic tyrosine kinase activity in the cytoplasmic domain of EGFR, which in turn leads to recruitment and phosphorylation of other substrates, resulting in mitogenic signaling and/or a variety of other cellular activities (Pawson and Schlessinger, *Curr. Biol.* 3:434-442, 1994; Alroy and Yarden, *FEBS Lett.* 410:83-86, 1997; Riese and Stern, *Bioessays* 20:41-48, 1998).

The EGFR is a target for therapeutic intervention for a diverse range of conditions. Overexpression of the EGFR is associated with many types of malignancies and often correlates with poor patient prognosis. Modulating EGFR activity has influenced clinical results in the treatment of cancers (Mendelsohn and Baselga, *Oncogene* 19:6550-6565, 2000). Stimulation of EGFR with EGF has also been shown to accelerate wound healing, (e.g., in gastric and oral ulcers, diabetic foot ulcers, skin grafts, corneal epithelial wounds, and tympanic membrane perforations (Milani and Calabro, *Microsc. Res. Tech.* 53:360-371, 2001; Fujisawa, et al., *J. Oral Pathol. Med.* 32:358-366, 2003; Bennett, et al., *Br J Surg.* 90:133-146, 2003; Brown, et al., *N. Engl. J. Med.* 321:76-79, 1989; Lu, et al., *Exp. Biol. Med.* (Maywood) 226:653-664, 2001; Ma, et al., *Acta Otolaryngol.* 122:586-599, 2002). EGF may also regulate nerve regeneration and atherogenesis (Xian and Zhou, *Mol. Neurobiol.* 20:157-183, 1999; Lamb, et al., *Atherosclerosis* 168:191-194, 2003).

SUMMARY

The present invention is based, in part, on our discovery that EGF can be engineered to generate mutants that bind to the EGF receptor (EGFR) of a cell and that have a desirable effect on the activity of the cell. For example, the mutants can agonize the receptor (i.e., increase a biological activity of the receptor), or antagonize the receptor (i.e., decrease or inhibit a biological activity of the receptor). In turn, the rate at which the cell proliferates, for example, can be changed. Some of the mutants bind an EGFR with a higher affinity than the corresponding wild-type EGF exhibits. The affinity may increase at least (or by about), for example, 2-, 5-, 10-, 15-, 20-, 25-, 30-, 50-, or 100-fold relative to wild-type EGF. As described further below, the mutant EGF polypeptides of the invention, or nucleic acid molecules that encode them, can be used in a variety of contexts including therapeutics (for the treatment of cancer, particularly EGFR-mediated cancers, for example), cosmetics (topical application of certain mutant EGF polypeptides is expected to improve the appearance of the skin), and veterinary applications (certain mutant EGF polypeptides can be administered as an alternative to shearing animals, such as sheep).

Accordingly, the invention features polypeptides (e.g., an isolated polypeptide) including a mutant of EGF (e.g., a human or ovine EGF), wherein the polypeptide: a) binds an epidermal growth factor receptor (EGFR (e.g., a cognate EGFR)) with an affinity that is, when tested under comparable conditions, substantially the same as or greater than (e.g., at least 2-5-fold greater than) the affinity with which a corresponding wild-type (wt) EGF (e.g., a human or ovine wt EGF) binds its EGFR; b) modulates an activity of the EGFR (e.g., alters a biological process mediated by receptor binding); and c) comprises the following sequence: $X_1$-$X_2$-$X_3$-$X_4$-$X_5$-C-P-$X_8$-$X_9$-$X_{10}$-$X_{11}$-G-$X_{13}$-C-L-$X_{16}$-$X_{17}$-G-$X_{19}$-C-$X_{21}$-Y-I-$X_{24}$-$X_{25}$-$X_{26}$-D-$X_{28}$-Y-$X_{30}$-C-$X_{32}$-C-$X_{34}$-$X_{35}$-G-Y-$X_{38}$-G-E-R-C-Q-Y-$X_{45}$-$X_{46}$-L-$X_{48}$-$X_{49}$-$X_{50}$-$X_{51}$-$X_{52}$-$R_{53}$ (SEQ ID NO:47), where X represents any amino acid residue (e.g., a naturally or non-naturally occurring amino acid residue) except cysteine (C). Thus, the invention encompasses polypeptides that are mutants of EGF but that include the sequence G-E-R-C-Q-Y (SEQ ID NO:48).

The mutant EGF sequences can differ from the variable sequence shown above or from a wild-type EGF sequence (e.g., SEQ ID NO:1) by a limited number of residues (e.g., 1-10 (e.g., 1, 2, 3, 4, 5, or 8 residues)). In such mutants, many of the residues in the wild-type EGF sequence would be retained. For example, a mutant EGF can include at least 15-40 residues (e.g., 15, 17, 19, 20, 30, or 40 residues) that are identical to the residues at corresponding positions in a wild-type EGF sequence (e.g., at least 15, 17, 19, 20, 30, or 40 residues in the sequence shown in SEQ ID NO:1). If desired, the extent of identity can be expressed as a percentage. For example, a mutant EGF polypeptide (e.g., a mutant of a human EGF polypeptide) can contain 10, 15, 17, 19, 20, 22, 25, 30, 35, or 40 (or at least 10, 15, 17, 19, etc. . . . ) residues that are identical to those at corresponding positions in a corresponding wild-type sequence. Retained residues can include one or more of the following: C at $X_6$, P at $X_7$, G at $X_{12}$, C at $X_{14}$, L at $X_{15}$, G at $X_{18}$, C at $X_{20}$, Y at $X_{22}$, I at $X_{23}$, D at $X_{27}$, Y at $X_{29}$, C at $X_{31}$, C at $X_{33}$, G at $X_{36}$, Y at $X_{37}$, G at $X_{39}$, E at $X_{40}$, R at $X_{41}$, C at $X_{42}$, Q at $X_{43}$, Y at $X_{44}$, L at $X_{47}$ (where the positions given (e.g., $X_6$) refer to positions in a corresponding wild-type EGF amino acid sequence (e.g., a human EGF sequence)).

With respect to affinity, a mutant EGF polypeptide can bind to an EGFR with a $K_D$ of equal to or less than about 20 nM; equal to or less than about 10 nM; equal to or less than about 5 nM; or equal to or less than about 1 nM. In one embodiment, the polypeptide binds to a human EGFR (although veterinary uses are also contemplated, as described above; a mutant EGF can be topically or systemically applied to shear animals, such as sheep).

In one embodiment, the residues of the mutant EGF that are non-identical to SEQ ID NO:1 are non-conserved residues between EGF paralogs. Examples of non-conserved residues between EGF paralogs are residues at positions 3, 4, 5, 8, 10, 16, 17, 21, 26, 28, 38, 45, 48, and 51 of SEQ ID NO:1. While the mutations can be substitution mutations (as implied here), they can also be mutations made by deleting or adding one or more amino acid residues to a wild-type EGF polypeptide. Where residues have been deleted, the mutant EGF polypeptide can include about or at least 45 amino acid residues (e.g., 45-52 amino acid residues).

As noted above, upon binding to an EGFR of a cell (e.g., a cell in vivo or maintained under physiological conditions or in cell culture), the mutant EGF polypeptide can modulate the activity of the cell. For example, the mutant EGF polypeptide can modulate tyrosine kinase activation (e.g., receptor tyrosine kinase phosphorylation of EGFR). In some instances, the mutant EGF enhances phosphorylation of EGFR in EGFR-expressing cells; in other instances, it inhibits such phosphorylation. Another activity (or event) that can be affected is the cell cycle (e.g., a mutant EGF polypeptide can arrest the cycle arrest or inhibit its progression; such mutants can be used as chemotherapeutic agents, to combat atherosclerosis, or in any other circumstance where there is excessive or unwanted cellular proliferation). Other mutant EGF polypeptides can stimulate progression through the cell cycle (proliferation can be assayed by standard techniques; the mutant EGF can be about 2.5, 5-, 10-, or 20-fold more mitogenic than wild-type EGF). A polypeptide that includes a mutant EGF that stimulates cell cycle progression can be used as a wound healing agent (which may facilitate the rate at which a wound heals or the extent to which it heals (e.g., the extent of repair and the quality of regenerated tissue (e.g., skin with improved functionality and/or appearance; such mutants may also be useful in regenerative medicine). Cell proliferation assays can be performed using colorimetric analysis of WST-8 uptake.

Another activity one can assay is the ability of a mutant EGF polypeptide to modulate apoptosis. While some of the mutants described herein can cause apoptosis of an EGFR-expressing cell (and are therefore useful in treating or ameliorating a symptom of a condition in which there is unwanted cellular proliferation, such as cancer or restenosis), others will inhibit apoptosis (and are therefore useful in treating or ameliorating a symptom of a condition in which cells are undesirably lost (e.g., a neurodegenerative or wasting disease)). A polypeptide that includes a mutant EGF that causes apoptosis can be used as a chemotherapeutic agent (whether one assays cellular proliferation or apoptosis, mutant EGF polypeptides that are useful in treating cancer may also be usefully applied to patients who are at risk of developing cancer (e.g., those with a family history (or a genetic predisposition as indicated by the a cancer-related gene), a prior occurrence (e.g. a prior tumor), or who have been exposed to an event that places them at risk (e.g., exposure to radiation))). The patient may have, for example, a low grade or moderate dysplasia. Mutant EGF polypeptides that stimulate apoptosis can also be used to treat (or to prevent or inhibit the development of) atherosclerosis. Assays of apoptosis (or of any other activity described herein) can be carried out with a mutant EGF polypeptide and an EGFR-expressing cell (or pluralities thereof). Appropriate controls, such as a parallel assay in the absence of the mutant EGF polypeptide or in the presence of a wild-type EGF polypeptide can be carried out for comparison.

The mutant EGF can include an amino acid change at least two of the following residues: $X_1$, $X_2$, $X_3$, $X_4$, $X_5$, $X_8$, $X_9$, $X_{10}$, $X_{11}$, $X_{13}$/$X_{16}$/$X_{17}$, $X_{19}$, $X_{21}$, $X_{24}$; $X_{25}$, $X_{26}$, $X_{28}$, $X_{30}$, $X_{32}$, $X_{34}$, $X_{35}$, $X_{38}$, $X_{45}$, $X_{46}$, $X_{48}$, $X_{49}$, $X_{50}$, $X_{51}$, or $X_{52}$ within the sequence $X_1$-$X_2$-$X_3$-$X_4$-$X_5$-C-P-$X_8$-$X_9$-$X_{10}$-$X_{11}$-G-$X_{13}$-C-L-$X_{16}$-$X_{17}$-G-$X_{19}$-C-$X_{21}$-Y-I-$X_{24}$-$X_{25}$-$X_{26}$-D-$X_{28}$-Y-$X_{30}$-C-$X_{32}$-C-$X_{34}$-$X_{35}$-G-Y-$X_{38}$-G-E-R-C-Q-Y-$X_{45}$-$X_{46}$-L-$X_{48}$-$X_{49}$-$X_{50}$-$X_{51}$-$X_{52}$-$R_{53}$ (SEQ ID NO:47). The amino acid change can be a substitution (which can be characterized as conservative or non-conservative; the substitution can also be of a non-naturally occurring amino acid residue). The amino acid change can be a substitution to an amino acid residue other than cysteine, and the mutant EGF can include 2, 3, 4, 5, 6, 7, 8, 9, 10, 11, or 12 amino acid changes relative to the corresponding wild-type sequence. Particular mutant EGF sequences can include changes at $X_{48}$, $X_{51}$, and/or $X_{52}$; changes at $X_1$ and/or $X_3$; or changes at $X_3$ and/or $X_{52}$. In addition to these mutants, one can introduce a mutation at any or all of $X_{16}$, $X_{28}$, and/or $X_{38}$.

The mutant EGF can include an amino acid change at least two of the following residues: $X_1$, $X_2$, $X_3$, $X_4$, $X_5$, $X_8$, $X_9$, $X_{10}$, $X_{11}$, $X_{13}$, $X_{16}$, $X_{17}$, $X_{19}$, $X_{21}$, $X_{24}$, $X_{25}$, $X_{26}$, $X_{28}$, $X_{30}$, $X_{32}$, $X_{34}$, $X_{35}$, $X_{38}$, $X_{45}$, $X_{46}$, $X_{48}$, $X_{49}$, $X_{50}$, $X_{51}$, or $X_{52}$ within the sequence $X_1$-$X_2$-$X_3$-$X_4$-$X_5$-C-P-$X_8$-$X_9$-$X_{10}$-$X_{11}$-G-$X_{13}$-C-L-$X_{16}$-$X_{17}$-G-$X_{19}$-C-$X_{21}$-Y-I-$X_{24}$-$X_{25}$-$X_{26}$-D-$X_{28}$-Y-$X_{30}$-C-$X_{32}$-C-$X_{34}$-$X_{35}$-G-Y-$X_{38}$-G-E-R-C-Q-Y-$X_{45}$-$X_{46}$-L-$X_{48}$-$X_{49}$-$X_{50}$-$X_{51}$-$X_{52}$-$R_{53}$. The amino acid change can be a substitution (which can be characterized as conservative or non-conservative; the substitution can also be of a non-naturally occurring amino acid residue). The amino acid change can be a substitution to an amino acid residue other than cysteine, and the mutant EGF can include 2, 3, 4, 5, 6, 7, 8, 9, 10, 11, or 12 amino acid changes relative to the corresponding wild-type sequence. Particular mutant EGF sequences can include changes at $X_{48}$, $X_{51}$, and/or $X_{52}$; changes at $X_1$ and/or $X_3$; or changes at $X_3$ and/or $X_{52}$. In addition to these mutants, one can introduce a mutation at any or all of $X_{16}$, $X_{28}$, and/or $X_{38}$.

In one embodiment, the mutant EGF comprises the following amino acid sequence: $X_1$-$X_2$-$X_3$-$X_4$-$X_5$-C-P-$X_8$-$X_9$-$X_{10}$-$X_{11}$-G-$X_{13}$-C-L-$X_{16}$-$X_{17}$-G-$X_{19}$-C-$X_{21}$-Y-I-$X_{24}$-$X_{25}$-$X_{26}$-D-$X_{28}$-Y-$X_{30}$-C-$X_{32}$-C-$X_{34}$-$X_{35}$-G-Y-$X_{38}$-G-E-R-C-Q-Y-$X_{45}$-$X_{46}$-L-$X_{48}$-$X_{49}$-$X_{50}$-$X_{51}$-$X_{52}$-$R_{53}$ (SEQ ID NO:49), wherein: a) $X_1$ is S, K, Y, T, or H; b) $X_2$ is G or R; c) $X_3$ is N, G, or Y; d) $X_4$ is P or F; e) $X_5$ is G or K; f) $X_8$ is P, S, or R; g) $X_9$ is P; h) $X_{10}$ is Y; i) $X_{11}$ is N, S, or E; j) $X_{13}$ is H; k) $X_{16}$ is Q or N; l) $X_{17}$ is G; m) $X_{19}$ is A; n) $X_{21}$ is V, R, or K; o) $X_{24}$ is K or G; p) $X_{25}$ is T; q) $X_{26}$ is V; r) $X_{28}$ is R, S, or T; $X_{30}$ is V; t) $X_{32}$ is S; u) $X_{34}$ is A; v) $X_{35}$ is A; w) $X_{38}$ is T, A, V, S, N, or L; x) $X_{45}$ is G, Q, or P; y) $X_{46}$ is G; z) $X_{48}$ is R or T; aa) $X_{49}$ is R; bb) $X_{50}$ is L; cc) $X_{51}$ is G, A, W, K, or Y; or dd) $X_{52}$ is P, R, or T. More specifically, the mutant EGF polypeptide can include 2, 3, 4, 5, 6, 7, 8, 9, 10, 11, or 12 amino acid changes from SEQ ID NO:1.

Specific mutant EGF sequences useful as described herein can include one of the following sequences:

```
                                              (SEQ ID NO: 2)
NSDSGCPLSHDGYCLHDGVCMYIEALDKYACNCVVGYTGERCQYRDLRWW

ELR;
                                              (SEQ ID NO: 3)
NSDSECPLSHDGYCLHGGVCMYIKAVDRYACNCVVGYIGERCQYRDLTWW

GPR;
```

-continued (SEQ ID NO: 4)
NSDSECPLSHDGYCLHDGVCVYIKTLDKYACNCVVGYAGERCQYRDLRWW
ELR;

(SEQ ID NO: 5)
SSNSGCPLSHDGYCLHDGVCMYIEALDRYACNCVVGYAGERCQYRDLKWW
ELR;

(SEQ ID NO: 6)
NSDSECPLSHDGYCLHDGACVYIEALDKYACNCVVGYVGERCQYRDLRWW
GRR;

(SEQ ID NO: 7)
NSGSECPLSHDGYCLHDGVCMYIEALDKYACNCVVGYIGERCQYRDLRWW
ELR;

(SEQ ID NO: 8)
NSDSEGPLSHDGYCLHDGACMYIEALDKYVCNCAVGYIGERCQYRDLRWW
GPR;

(SEQ ID NO: 9)
NGDSECPLSYDGYCLHDGVCMYIEALDKYACNCVVGYIGERCQYRDLKWW
ERR;

(SEQ ID NO: 10)
NSDSECPLSHDGYCLHDGVCMYIEALDRYACNCVVGYIGERCQYRDLRWW
ELR;

(SEQ ID NO: 11)
NSDSECPLSHNGYCLHDGVCMYIKALDKYACNCVAGYTGERCQYRDLRWW
GLR;

(SEQ ID NO: 12)
NSDSECPLSHDGYCLHDGVCMYIEALDKYACNCVVGYAGERCQYRDLRWW
ARR;

(SEQ ID NO: 13)
NSGSKCPLSHDGYCLHDGVCMYIGALDRYACNCVVGYVGERCQYRDLRWW
ELR;

(SEQ ID NO: 14)
KSGPGCPPPYDGYCLQGGVCMYIGALDRYACNCVVGYIGERCQYRDLKWW
EPR;

(SEQ ID NO: 15)
NSDSECPLSHDGYCLHDGVCMYIKALDKYACNCVVGYTGERCQYRDLRWW
GRR;

(SEQ ID NO: 16)
YSDSECPLSHDGYCLHDGVCMYIEALDKYACNCVVGYAGERCQYRDLRWW
ELR;

(SEQ ID NO: 17)
NSNSECPLSHDGYCLHDGVCRYIEALDRYACNCVVGYIGERCQYGDLRWW
GRR;

(SEQ ID NO: 18)
SRGSKCPPSHDGYCLQGGVCMYIEALDRYACNCVVGYAGERCQYRDLTWW
GRR;

(SEQ ID NO: 19)
NSDSGCPLSHSGYCLHDGVCMYIKALDRYACNCVVGYAGERCQYRDLRWW
ARR;

(SEQ ID NO: 20)
SSGSERPPSHDGHCLHGGVCMYIEALDKYACSCAVGYTGERCQYRGLRWW
GLR;

(SEQ ID NO: 21)
NSDSECPPSHDGYCLQGGVCMYIEALDRYACNCVVGYIGERCQYRDLTWW
EPR;

(SEQ ID NO: 22)
TRGSECPLSHDGYCLHDGVCMYIGALDRYACNCVVGYTGERCQYRDLRWW
ARR;

(SEQ ID NO: 23)
NSDFGCPLSYDGYCLHDGVCMYIKALDKYACNCVVGYAGERCQYRDLRWW
GRR;

(SEQ ID NO: 24)
SRGSKCPPSHDGYCLHDGVCMYIEALDRYACNCVVGYAGERCQYRDLRWW
ARR.

(SEQ ID NO: 25)
SSGSECPSSHDGYCLHDGACMYIEALDRYACNCAVGYAGERCQYRDLRWW
GRR;

(SEQ ID NO: 26)
SSNSECPPSHDGYCLHDGVCMYIEALDRYACNCVVGYAGERCQYRDLRWW
ARR;

(SEQ ID NO: 27)
NSYSECPLSHDGYCLHGGVCRYIEALDKYACNCVVGYSGERCQYRDLRWW
GLR;

(SEQ ID NO: 28)
NSGSECPLSYDGYCLHGGVCMYIEALDRYACNCVVGYNGERCQYRDLKWW
WLR;

(SEQ ID NO: 29)
NSNSECPLSHDGYCLNDGVCRYIEALDKYACNCVVGYVGERCQYRDLRRW
ELR;

(SEQ ID NO: 30)
NSGSECPLSYDGYCLNDGVCMYIGALDKYACNCVVGYTGERCQYQDLRWW
KLR;

(SEQ ID NO: 31)
HSNSECPLSHDGYCLNDGVCMYIKALDTYACNCVVGYVGERCQYPDLKWW
GLR;

(SEQ ID NO: 32)
NSYSECPLSYDGYCLNDGVCRYIEALDRYACNCVVGYIGERCQYRDLKWW
WLR;

(SEQ ID NO: 33)
SRGSKCPPSHDGYCLNDGVCMYIEALDKYACNCVVGYLGERCQYRDLKWW
YTR;

(SEQ ID NO: 34)
NSDPKCPLSHEGYCLNDGVCMYIGTLDRYACNCVVGYVGERCQYRDLKWL
ALR;

(SEQ ID NO: 35)
NSNSECPLSHDGYCLNDGVCKYIEALDRYACNCVVGYAGERCQYRDLRWW
GLR;

-continued

NSYSECPPSYDGYCLHDGVCRYIEALDSYACNCVVGYAGERCQYRDLRWW (SEQ ID NO: 36)
GRR;

NSNSECPRSHDGYCLNDGVCMYIEALDRYACNCVVGYVGERCQYRDLRWW (SEQ ID NO: 37)
GLR;
and

SSGSECPLSHDGYCLNDGVCMYIEALDKYACNCVVGYVGERCQYRDLRWW (SEQ ID NO: 38)
ARR.

While the invention is not limited to mutants discovered by any particular mechanism, these mutants were discovered by directed evolution through yeast surface display (those exhibiting enhanced affinity for the EGFR were are biased toward substitution at positions exhibiting significant phylogenetic variation whereas loss-of-function mutants were biased toward highly conserved positions). More specifically, the invention encompasses the affinity enhanced mutant EGF polypeptides in which Tyr13, Tyr22, and Tyr37 of SEQ ID NO:1 or corresponding residues in a non-human EGF are retained (as in the wild-type polypeptide); mutant EGF polypeptides in which Leu47 and Arg 41 of SEQ ID NO:1 or corresponding residues in a non-human EGF are retained (as in the wild-type polypeptide); and mutant EGF polypeptides in which a small hydrophobic residue is retained at position 30 (e.g., Ala), and large hydrophobic residues are retained at positions 23 and 26 (e.g., Ile or Leu) of SEQ ID NO:1 or at corresponding residues in a non-human EGF. In other embodiments, one to 14 amino acid residues are mutant. In polypeptides limited in that manner or mutant to a different extent, the residues retained can be one or more of those at positions 41, 46, 13, 15, 16, 18, and 39 of SEQ ID NO:1.

The mutant EGF (e.g., a mutant EGF described herein) can be modified to increase stability (e.g., by removing the C-terminal R, or by adding an amino acid sequence). The mutant EGF can further include a label, a cytotoxin, and/or a carrier.

In another aspect, the invention features a physiologically acceptable composition including a polypeptide including a mutant EGF polypeptide or a mutant EGF nucleic acid sequence as described herein. The composition can further include a pharmaceutical carrier, excipient, or diluent. As noted above, certain mutant EGF polypeptides can be used in cosmetic applications and will be appropriately formulated for such applications. For example, the composition can include any of the ingredients used in lotions and creams (e.g., vitamins, plant extracts, lipids, retinols, and the like). Other mutants will have activities suitable for use in more serious health-related contexts, such as cancer, atherosclerosis (including restenosis), and wound healing. The formulations generated using such mutants will include those suitable for oral or parenteral administration, as described further below. Whether intended for cosmetic application or in wound healing, the present mutants can be assessed for an ability to promote neovascularization, organization by fibroblasts, and collagen accumulation.

In another aspect, the invention features a compound (or composition) including a mutant EGF polypeptide described herein and a non-polypeptide moiety that is physically associated with (e.g., covalently or non-covalently joined to) the polypeptide (e.g., a polymer such as PEG). Mutant EGF polypeptides fused to an Aga2p agglutinin subunit are within the scope of the present invention.

In another aspect, the invention features an isolated nucleic acid molecule including a sequence that encodes the mutant EGF described herein. The nucleic acids can be optimized for expression in a particular cell type (e.g., by using codons used in highly expressed proteins in that cell type).

The invention also features an expression vector that includes a nucleic acid having a sequence encoding a mutant EGF described herein. Host cells including such nucleic acid sequences are also within the scope of the present invention (e.g., a prokaryotic cell such as E. coli, a eukaryotic cell such as a mammalian cell (e.g., a CHO cell or a fibroblast) or a yeast cell).

In another aspect, the invention features kits including a mutant EGF described herein or a nucleic acid encoding the mutant EGF and instructions for diagnostic or therapeutic use.

In another aspect, the invention features a method of modulating an EGFR activity in a cell (including a cell in culture or a cell in vivo (e.g., within a human patient)). The method includes, for example, identifying a cell or subject in need of treatment and administering a polypeptide including a mutant EGF to the cell or subject. The polypeptide is administered under conditions (e.g., at physiologically acceptable temperature and pH) and in an amount sufficient to modulate the activity of the EGFR in the cell, to thereby modulate an EGFR activity in the subject, to a clinically beneficial extent. The mutant EGF polypeptide used in the methods of the invention can be one that a) binds an epidermal growth factor receptor (EGFR) with an affinity that is at least 2-5-fold greater than the affinity with which wild-type (wt) EGF binds the EGFR; b) modulates an activity of the EGFR; and c) comprises the following sequence: $X_1$-$X_2$-$X_3$-$X_4$-$X_5$-C-P-$X_8$-$X_9$-$X_{10}$-$X_{11}$-G-$X_{13}$-C-L-$X_{16}$-$X_{17}$-G-$X_{19}$-C-$X_{21}$-Y-I-$X_{24}$-$X_{25}$-$X_{26}$-D-$X_{28}$-Y-$X_{30}$-C-$X_{32}$-C-$X_{34}$-$X_{35}$-G-Y-$X_{38}$-G-E-R-C-Q-Y-$X_{45}$-$X_{46}$-L-$X_{48}$-$X_{49}$-$X_{50}$-$X_{51}$-$X_{52}$-$R_{53}$ (SEQ ID NO:47), where X represents any amino acid residue except cysteine (C). The cell can be one in a subject (e.g., a human patient or another mammal, such as a sheep, goat, llama, horse, pig, or cow), and the mutant EGF polypeptide can be administered locally (e.g., topically (as to a wound)) or systemically.

The methods of the invention can be carried out with mutant EGF polypeptides that are antagonists of an EGFR activity, agonists of an EGFR activity, or superagonists of an EGFR activity. Where the method is applied to a cell that is proliferating, the cell can be one that overexpresses an EGFR (as can occur in tumor cells).

In the event the cell is within a patient who has cancer, that cancer can be any cancer that is associated with activation of the EGFR (e.g., an epithelial cancer or a cancer that affects the nervous system). Mutant EGF polypeptides useful in the treatment of unwanted cellular proliferation (i.e. those that inhibit such activity) include those in which the mutant EGF polypeptide further comprises an agent that lyses or otherwise kills the cell (e.g. a cytotoxin. (e.g., diphtheria toxin)). Moreover, the mutant EGF polypeptides of the invention can be administered in combination with a second agent (e.g., a chemotherapeutic agent or a polypeptide agent). The second agent can also be a polypeptide (e.g., an antibody or antigen-binding fragment thereof). Thus, the instant invention includes methods of promoting localized delivery of chemotherapeutic or other therapeutic agents. Once associated with a mutant EGF, the EGF can serve as a targeting moiety for EGFR-bearing cells, which will take up the EGF and an agent to which it is bound (e.g., by receptor-mediated endocytosis).

In one embodiment, the subject has a wound (e.g., an ulcer, such as a gastric ulcer, an oral ulcer, or an ulcer on an extremity (e.g., a diabetes-associated foot ulcer)). The wound can be generated accidentally (as by trauma, including burn trauma) or by an intention procedure such as a surgical procedure (e.g., a skin grafting procedure). Epidermal wounds and corneal epithelial wounds can also be treated according to the methods of the present invention, as can tympanic membrane perforations and nerve injuries.

In another aspect, the invention features a method of treating a coronary disorder in a subject. As with related methods of the invention, the method includes, for example: administering a therapeutically effective amount of a polypeptide including a mutant EGF (e.g., a mutant EGF described herein) to a subject. The coronary disorder or disease can be atherogenesis.

In another aspect, the invention features a method for stimulating cell growth in a subject. The method includes, for example: administering a therapeutically effective amount of a polypeptide including a mutant EGF (e.g., a mutant EGF described herein) to a subject. This method can be applied to stimulate the growth of islet cells of the pancreas.

In another aspect, the invention features a method for delaying cutaneous cell atrophy in a subject. The method includes, for example: administering a therapeutically effective amount of a polypeptide including a mutant EGF (e.g., a mutant EGF described herein) to the subject.

In another aspect, the invention features a method for modulating hair growth in a subject. The method includes, for example: administering a therapeutically effective amount of a polypeptide including a mutant EGF (e.g., a mutant EGF described herein) to the subject.

In another aspect, the invention features methods of modulating an EGFR activity in a cell by, for example, administering a nucleic acid encoding a polypeptide including a mutant EGF (e.g., a mutant EGF described herein) to the cell, and expressing the nucleic acid in the cell. The nucleic acid can be contained within a vector or host cell, and the indications for use include those described herein in connection with the polypeptide.

In another aspect, the invention features a method for producing a mutant EGF. The method includes for example: providing a nucleic acid encoding a mutant EGF (e.g., a mutant EGF described herein), expressing the nucleic acid in the host cell, and isolating the mutant EGF expressed by the cell.

In another aspect, the invention features a method for identifying a mutant EGF polypeptide that binds to an EGFR with an affinity greater than that of wild-type EGF. The method includes, for example: a) providing a library of nucleic acids encoding a plurality of mutant EGF polypeptides; b) expressing the nucleic acids encoding the plurality of mutant EGF polypeptides; c) evaluating binding of EGFR to the plurality of mutant EGF polypeptides; and d) selecting those mutant EGF polypeptides that bind to the EGFR with an affinity greater than that of wild-type EGF. One can evaluate binding to EGFRs expressed on cells (e.g., fibroblast cells).

In another aspect, the invention features a mutant EGF polypeptide produced by a method that includes: a) providing a library of nucleic acids encoding a plurality of mutant EGF polypeptides; b) expressing the nucleic acids encoding the plurality of mutant EGF polypeptides; c) evaluating binding of EGFR to the plurality of mutant EGF polypeptides; and d) selecting those mutant EGF polypeptides that bind to the EGFR with an affinity greater than that of wild-type EGF.

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes. U.S. Ser. No. 60/784,274 is incorporated by reference in its entirety for all purposes.

DESCRIPTION OF DRAWINGS

FIG. 1 is a depiction of amino acid sequences of a wild-type EGF (EGF wt; SEQ ID NO:1) and first generation EGF mutants (SEQ ID NOs 2-13, respectively).

FIGS. 2A-B depict amino acid sequences of wild-type EGF (SEQ ID NO:1) and second generation EGF mutants. FIG. 2A depicts mutants produced by mutagenesis and DNA shuffling (SEQ ID NOs 14-24, respectively). FIG. 2B depicts mutants produced by DNA shuffling, mutagenesis, and oligo doping (SEQ ID NOs 25-38, respectively).

FIG. 3 is an alignment of the amino acid sequence wild-type human EGF (SEQ ID NO:1) with EGF orthologs from various species (SEQ ID NOs 39-46, respectively). Amino acid mutations generated by mutagenesis that are present in the orthologs are shaded in gray.

FIG. 4 is a depiction of the amino acid sequence of wild-type human EGF (SEQ ID NO:1). Positions mutagenized in other studies are shaded in gray. The site-directed and randomized mutations made previously are indicated beneath the sequence.

DETAILED DESCRIPTION

Figure 5:
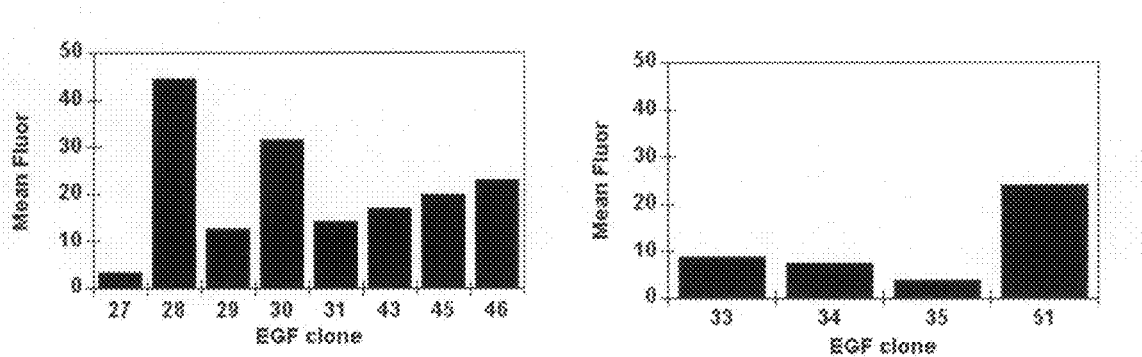
FIG. 5 is a pair of bar graphs generated by binding studies with first generation EGF mutants (clones 27, 28, 29, 30, 31, 43, 45, 46, 33, 34, 35, and 51). Binding of EGF mutants displayed on yeast to soluble EGFR. EGF mutants isolated from the library screens were expressed on the surface of yeast and treated with soluble fluorescent EGFR. Fluorescence intensity of cell surface labeling was measured by flow cytometry.

EGF mutants that bind to the EGFR and modulate its activity (by acting as receptor agonists or antagonists) can be used in the prevention and treatment of many diverse conditions, including cancers, topical and mucosal ulcers, conditions that involve nerve damage, and atherosclerosis. We based our efforts toward generating useful mutants on structure-function analyses of EGF and EGFR. Sequence conservation among species, structural considerations, and reports with peptide fragments, were used to propose residues of EGF that were important for interaction with the EGFR. In addition, an EGF surface patch defined by residues Y13/L15/H16, and R41/Q43/L47 had been proposed to be involved in high affinity binding (Campbell et al., *Prog. Growth Factor Res.* 1:13-22, 1989). Site-directed mutagenesis of these positions demonstrated key residues that appeared to be important for receptor interaction or protein integrity. Based on these findings, several groups have attempted to engineer EGF for higher affinity, and hence biological potency by focusing on these residues (FIG. 4). In one study, phage displayed libraries of EGF randomized at positions R41 or D46 failed to identify affinity improved EGF mutants (Souriau et al., *Nucleic Acids Res.* 25:1585-1590, 1997). Similarly, randomization at positions Y13, L15, and H16 demonstrated that these positions were optimized for binding and activity (Souriau et al., *Biol. Chem.* 380:451-458, 1999). Limited success was obtained by site-directed mutagenesis of EGF G12Q, H16D, H16A, Y13W, Q43A, and L15A (Mullenbach et al., *Protein Eng.* 11:473-480, 1998). The mutant G12Q was reported to have a five-fold increase in binding and activation over wt EGF. Another study reported the generation of EGF mutants that bind 30-fold more effectively as compared to wt EGF, but did not demonstrate dose-dependency or biological activity. The same study also described a mutant that bound more weakly to the receptor than wt, but which exhibited biological potency analogous to wt (Coco et al., *Nature Biotechnol.* 20:1246-1250, 2002).

Many of the affinity-enhancing EGF mutations described herein are biased towards those found in EGF orthologs (and paralogs) and generally do not occur in conserved regions of the protein (FIG. 3). Other mutagenesis studies have focused on amino acids of the EGF that are highly conserved among the EGF orthologs. Contrary to other EGF mutants reported to have an enhanced affinity for the receptor, the mutants described herein have enhanced biological potency.

Mutant EGF Polypeptides

The invention features mutant EGF polypeptides that can function as agonists or antagonists of wild-type EGF. Accordingly, the mutants will bind an EGFR, and may do so with an affinity that is greater than that with which the corresponding wild-type EGF binds the receptor. Although we use the term "polypeptide" to describe our mutants, the use of that term is not meant to distinguish the present compositions from a "protein" or "peptide" (unless specifically noted, we consider all of these terms to refer to any chain of amino acid residues, regardless of length or post-translational modification (e.g., glycosylation or phosphorylation)). The mutant EGF polypeptides of the invention can be "substantially pure," meaning that they can be separated from a cell (e.g., a host cell in which they are expressed); a sample constitutes a sample of "substantially pure" EGF polypeptide when it contains at least 60% by weight (dry weight) the polypeptide of interest (i.e., the mutant EGF polypeptide). Preferably, at least 75% of the sample (e.g., 80%, 85%, 90%, or more), by weight, is the mutant polypeptide of interest. Purity can be measured by any appropriate standard method (e.g., by column chromatography, polyacrylamide gel electrophoresis, or HPLC analysis).

EGF and its receptor have been identified in many species, including humans (see, e.g., Carpenter and Cohen, *Ann. Rev. Biochem.* 48:193-216, 1979). The mutant polypeptides of the present invention differ in sequence from the corresponding wild-type EGF and bind the EGFR with higher affinities than a wild-type EGF. For example, a mutant EGF polypeptide can have at least one mutation (e.g., a substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38 amino acid residues, and/or a deletion or addition of 1, 2, 3, 4, 5, 6, 7, 8, 9, 10, 11, 12, 13, 14, 15, or 16 amino acid residues) relative to the corresponding wild-type EGF. As this describes many possibilities, we note that the mutant EGF must have particular functional abilities as well; it must bind and modulate the activity of the EGFR, as described further below. For example, a mutant human EGF polypeptide is a polypeptide that differs from a wild-type human EGF in the manner described herein and that binds a human EGFR with an affinity that is greater than that with which the human wild-type EGF binds the receptor; a mutant murine EGF polypeptide differs from a wild-type murine EGF in the manner described herein and binds a murine EGFR with an affinity that is greater than that with which the murine wild-type EGF binds the receptor; and so forth.

In some embodiments, the invention includes mutant EGF polypeptides that bind EGFR with at least or about 2.0- (e.g. 2.5-, 3.0-, or 3.5-), at least or about 5.0- (e.g., 5.5-, 6.0-, or 6.5) at least or about 7.5- (e.g., 8.0- or 9.0-), at least or about 10.0- (e.g., 11.0-, 12.0-, or 13.0-), at least or about 15.0- (e.g., 17.0-, 18.0-, or 19.0-), at least or about 20.0- (e.g., -25.0), at least or about 30.0- (e.g., 30.0-, 35.0-, or 40.0-), or at least or about 50-fold higher affinity than the corresponding wild-type EGF polypeptide. Affinity can be measured with assays known in the art. Any given mutant EGF polypeptide can also have increased potency in an assay that measures an activity of EGFR. Like the property of affinity, the ability of a mutant EGF polypeptide to modulate EGFR activity can be assessed by numerous assays, including the binding and phosphorylation detection assays described herein. The effect on receptor activity can be to any appreciable extent; mutant EGF polypeptides are within the scope of the present invention so long as they have an increased binding affinity and modulate receptor activity to a degree that is clinically beneficial (e.g., to a degree that makes them useful in a diagnostic assay, screen, or therapeutic application).

The mutant polypeptides of the invention can be described as having a particular percent identity to wild-type EGF polypeptides. When examining the percent identity between two polypeptides, the length of the sequences compared will generally be at least 37 amino acids (e.g., 40, 45, or 50 amino acids), and can be the entire polypeptide (in this case, 53 amino acid residues).

The term "identity," as used herein in reference to polypeptide sequences, refers to the subunit sequence identity between two molecules. When a subunit position in both of the molecules is occupied by the same monomeric subunit (i.e., the same amino acid residue), then the molecules are identical at that position. The similarity between two polypeptides is a direct function of the number of identical positions. Sequence identity can frequently be determined by aligning two sequences "by eye" (we anticipate this can be done with many of the EGF mutants of the present invention). If necessary, sequence identity can also be measured using sequence analysis software. A mutant EGF polypeptide of the present invention can be one that is at least or about 65% identical (e.g., 70%, 75%, 80%, 85%, 90%, 95%, or 98%) to the corresponding wild-type EGF polypeptide. For example, a mutant EGF polypeptide in which 52 of 53 residues are identical to those in the wild-type EGF polypeptide would be about 98% identical to the wild-type polypeptide. These percentages can be calculated, if necessary, with the Sequence Analysis Software Package of the Genetics Computer Group at the University of Wisconsin Biotechnology Center (1710 University Avenue, Madison, Wis. 53705), with the default parameters thereof.

The mutation can consist of a change in the number or content of amino acid residues. For example, the mutant EGF can have a greater or a lesser number of amino acid residues than wild-type EGF (e.g., a small number of amino acid residues (e.g., 1-2, 2-5, 5-10, or 10-25 residues) can be added to, or deleted from, the C- or N-terminal). Alternatively, or in addition, the mutant polypeptide can contain a substitution of one or more amino acid residues that are present in the wild-type EGF (e.g., a mutant EGF polypeptide can include 2-12 residues that differ from those in the corresponding wild-type sequence and can (but do not necessarily) also include an addition or deletion of a small number of amino acid residues). While a number of residues can vary, "single" mutants are also within the scope of the present invention (the mutant EGF polypeptide can differ from wild-type EGF by the addition, deletion, or substitution of a single amino acid residue, for example, a substitution of the residue at position 48). The mutations can occur at any point in the sequence. For example, the mutations can occur at one or more of the following positions: 1, 2, 3, 4, 5, 8, 9, 10, 11, 13, 16, 17, 19, 21, 24, 25, 26, 28, 30, 32, 34, 35, 38, 45, 46, 48, 49, 50, 51, and 52 of SEQ ID NO:1 (wild-type human EGF). More specifically, the mutation can be a substitution of: S, K, Y, T, or H for the N at $X_1$ (the first amino acid residue of SEQ ID NO:1, which is N); G or R for the S at $X_2$; N, G, or Y for the D at $X_3$; P or F for the S at $X_4$; G or K for the E at $X_5$; P, S, or R for the L at $X_8$; P for the S at $X_9$; Y for the H at $X_{10}$; N, S, or E for the D at $X_{11}$; H for the Y at $X_{13}$; Q or N for the H at $X_{16}$; G for the D at $X_{17}$; A for the V at $X_{19}$; V, R, or K for the M at $X_{21}$; K or G for the E at $X_{24}$; T for the A at $X_{25}$; V for the L at $X_{26}$; R, S, or T for the K at $X_{28}$; V for the A at $X_{30}$; S for the N at $X_{32}$; A for the V at $X_{34}$; A for the V at $X_{35}$; T, A, V, S, N, or L for the I at $X_{38}$; G, Q, or P for the R at $X_{45}$; G for the D at $X_{46}$; R or T for the K at $X_{48}$; R for the W at $X_{49}$; L for the W at $X_{50}$; G, A, W, K, or Y for the E at $X_{51}$; and/or P, R, or T for the L at $X_{52}$. More specifically, the mutant EGF polypeptide can differ from wild-type EGF as shown in Table I (FIG. 1), Table II (FIG. 2A), or Table III (FIG. 2B). The nucleic acid sequence encoding the mutant EGF polypeptide can include one or more of the codons depicted in Tables IV and V.

Any of the substituted amino acid residues can be, but are not necessarily, conservative substitutions. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Non-conservative substitutions are typically substitutions between the groups above.

The mutant polypeptides of the instant invention can be produced synthetically or by expression of a recombinant nucleic acid molecule. For example, the polypeptides can be produced in eukaryotic organisms or synthesized in E. coli or other prokaryotes. In the event the polypeptide is a chimera (that includes, in addition to the mutant EGF, for example, a label or tag), it can be encoded by a hybrid nucleic acid molecule containing one sequence that encodes the mutant EGF and a second sequence that encodes a second polypeptide. For example, the mutant EGF polypeptide may be fused to a hexa-histidine tag to facilitate purification of bacterially expressed protein, or to a hemagglutinin tag to facilitate purification of protein expressed in eukaryotic cells.

The techniques that are required to make mutant EGF polypeptides are routine in the art, and can be performed without resort to undue experimentation by one of ordinary skill in the art. For example, a mutation that consists of a substitution of one or more of the amino acid residues in EGF (e.g., a human EGF) can be created using a PCR-assisted mutagenesis technique (e.g., as known in the art and/or described herein). Mutations that consist of deletions or additions of amino acid residues to an EGF polypeptide can also be made with standard recombinant techniques. In the event of a deletion or addition, the nucleic acid molecule encoding EGF can simply be digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated.

As noted above, the mutant EGF polypeptides can also be prepared as fusion or chimeric polypeptides that include a mutant EGF polypeptide and a heterologous polypeptide (i.e., a polypeptide that is not EGF or a mutant thereof) as described, for example, in U.S. Pat. No. 6,451,308. The heterologous polypeptide can serve any desired function. For example, it can increase the circulating half-life of the chimeric polypeptide in vivo. The polypeptide that increases the circulating half-life may be a serum albumin, such as human serum albumin, or the Fc region of the IgG subclass of antibodies. The Fc region can include a mutation that inhibits complement fixation and Fc receptor binding, or it may be lytic (i.e., able to bind complement or to lyse cells via another mechanism, such as antibody-dependent complement lysis (ADCC; see, e.g., Morrison et al., *The Immunologist* 2:119-124, 1994; and Brekke et al., *The Immunologist* 2:125, 1994). The Fc region can be a naturally occurring or synthetic polypeptide that is homologous to the IgG C-terminal domain produced by digestion of IgG with papain. The mutant EGF polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases.

In other embodiments, the chimeric polypeptide can include the mutant EGF polypeptide and a polypeptide that functions as an antigenic tag, such as a FLAG sequence. FLAG sequences are recognized by biotinylated, highly specific, anti-FLAG antibodies, as described herein (see also Blanar et al., *Science* 256:1014, 1992; LeClair et al., *Proc. Natl. Acad. Sci. USA* 89:8145, 1992). In some embodiments, the chimeric polypeptide further comprises a C-terminal c-myc epitope tag. Any other polypeptide used in the art to facilitate purification, to identify or localize a binding site, or to lyse or otherwise inhibit the activity of a cell can be fused or otherwise joined (e.g., chemically conjugated) to a mutant EGF (e.g., a mutant human EGF). In other embodiments, the chimeric polypeptide includes the mutant EGF and a polypeptide that functions to enhance expression or direct cellular localization of the mutant EGF polypeptide, such as the Aga2p agglutinin subunit (see, e.g., Boder and Wittrup, *Nature Biotechnol.* 15:553-7, 1997), which is incorporated herein by reference in its entirety.

Chimeric polypeptides can be constructed using no more than conventional molecular biological techniques, which are well within the ability of those of ordinary skill in the art to perform.

Nucleic Acid Molecules Encoding Mutant EGF Polypeptides

A mutant EGF polypeptide, either alone or as a part of a chimeric polypeptide, such as those described above, can be obtained by expression of a nucleic acid molecule; such nucleic acid molecules are within the scope of the invention. Just as mutant EGF polypeptides can be described in terms of their identity to wild-type EGF polypeptides, the nucleic acid molecules encoding them will necessarily have a certain identity with those that encode wild-type EGF. For example, the nucleic acid molecule encoding a mutant EGF polypeptide can be at least 65%, at least 75%, at least 85%, or at least 95% (e.g., 99%) identical to the nucleic acid encoding wild-type EGF (e.g., SEQ ID NO:1). For nucleic acids, the length of the sequences compared will generally be at least or about 110 nucleotides (e.g., at least or about 130 nucleotides, 150 nucleotides, or 159 nucleotides).

The nucleic acid molecules of the invention can vary but, due to the degeneracy of the genetic code, encode the same mutant EGF. The nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules of the invention may be referred to as "isolated" when they are within, for example, an expression vector (e.g., a plasmid or viral vector). The nucleic acids, whether within an expression vector or not, can also include some or all of the non-coding sequences that lies upstream or downstream from a sequence that naturally encodes EGF. For example, the mutant EGF nucleic acids of the invention can be operably linked to regulatory sequences (such as a promoter or enhancer) that normally influence the expression of a wild-type EGF. Those of ordinary skill in the art of molecular biology are familiar with routine procedures for isolating or otherwise producing nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription. Naturally occurring sequences can then be mutated (by, for example, the procedures described here) to produce the mutant EGF polypeptides of the invention. The nucleic acid molecules of the invention can be obtained by introducing a mutation into EGF-encoding DNA obtained from any biological cell, such as the cell of a mammal. Thus, the nucleic acids of the invention can be those of a mouse, rat, guinea pig, cow, sheep, horse, pig, rabbit, monkey, baboon, dog, or cat. Typically, the nucleic acid molecules will be those of a human.

As described above, the mutant EGF polypeptide of the invention may exist as a part of a chimeric polypeptide. Accordingly, a nucleic acid molecule of the invention can contain sequences encoding the heterologous polypeptide (e.g., the "marker" or "reporter"). Examples of marker or reporter genes include β-lactamase, chloramphenicol acetyltransferase (CAT), adenosine deaminase (ADA), aminoglycoside phosphotransferase (neo", G418"), dihydrofolate reductase (DHFR), hygromycin-B-hosphotransferase (HPH), thymidine kinase (TK), lacz (encoding β-galactosidase), and xanthine guanine phosphoribosyltransferase (XG-PRT). As with many of the standard procedures associated with the practice of the invention, skilled artisans will be aware of additional useful reagents, for example, of additional sequences that can serve the function of a marker or reporter.

Generation and Screening of Mutant EGF Polypeptides

Mutant EGF polypeptides can be generated by any of the methods known in the art for generating mutant sequences. For example, one can use directed mutagenesis, random mutagenesis (e.g., random PCR mutagenesis), DNA shuffling, or a combination of these techniques. An exemplary method for generating and screening a library of mutant EGF polypeptides can be carried out as follows. A wild-type EGF (e.g., human) coding sequence is subjected to random mutagenesis by error-prone polymerase chain reaction (PCR). The error rate is controlled by varying cycles of PCR amplification in the presence of nucleotide analogs 8-oxodGTP and dPTP (Zaccolo & Gherardi, *J. Mol. Biol.* 285: 775-83, 1999; Zaccolo et al., *J. Mol. Biol.*, 255:589-603, 1996). The PCR product obtained is further amplified by PCR without the nucleotide analogs. The final PCR product is transformed into yeast together with linearized, gapped plasmid that mediates homologous recombination in yeast. Homologous recombination in vivo in yeast between the 5' and 3' flanking 50 base pairs of the PCR product with the gapped plasmid produce a library of variants (Raymond et al., *Biotechniques* 26:134-8, 140-1, 1999).

A soluble ectodomain of EGFR is expressed in insect cell culture, purified and biotinylated. The mutant EGF is expressed as an Aga2p protein fusion in *Saccharomyces cerevisiae* EBY100 by induction in medium containing galactose (Boder & Wittrup, *Nat. Biotechnol.* 15:553-7, 1997). Yeast cells are labeled with antibody or biotinylated soluble EGFR (See, e.g., Boder & Wittrup, *Methods Enzymol.* 328: 430-44, 2000).

Yeast cells from the library are labeled with biotinylated soluble EGFR at 37° C., at a concentration of 0.2-0.8 nM, and saturating concentration of antibody that binds EGFR. The cells are washed, labeled with a fluorescent reagent that detects the antibody and a second fluorescent agent containing streptavidin. The cells are then sorted by flow cytometry. After the four rounds of sorting, DNA from individual is extracted, for example, using the Zymoprep kit (Zymo Research corporation). The DNA is amplified in bacteria and sequenced.

Second generation mutants can be generated by subjecting first generation mutants to DNA shuffling. See, e.g., U.S. Pat. No. 6,613,514 and references therein. Briefly, related nucleic acid sequences are fragmented, for example, by digestion with a nuclease, denatured by heat, renatured, and incubated with a DNA polymerase. This cycle is repeated from two to 100 times. Specific oligonucleotides containing desired mutations can be added, or "doped" into the reaction.

Mutant EGF polypeptides are assayed for biological potency (or activity). Any method by which one can evaluate EGFR phosphorylation, EGFR kinase activity, kinase activity of a substrate of EGFR, cell division, cell survival, and any parameter related to EGFR activity (whether that be on a cellular level or a systemic level), can be used to determine the biological potency (or activity) of any given mutant EGF polypeptide.

Expression of Mutant EGF Gene Products

The nucleic acid moleculese encoding a mutant EGF can be contained within a vector that is capable of directing their expression in, for example, a cell that has been transduced with the vector. Accordingly, in addition to mutant EGF polypeptides, expression vectors containing a nucleic acid molecule encoding a mutant EGF polypeptide and cells transfected with these vectors are within the scope of the invention.

Vectors suitable for use in the present invention include T7-based vectors for use in bacteria (see, for example, Rosenberg et al., *Gene* 56:125, 1987), the pMSXND expression vector for use in mammalian cells (Lee and Nathans, *J. Biol. Chem.* 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

Prokaryotic or eukaryotic cells that contain and express a nucleic acid molecule that encodes a mutant EGF polypeptide are also features of the invention. A cell of the invention is a transfected cell, i.e., a cell into which a nucleic acid molecule, for example a nucleic acid molecule encoding a mutant EGF polypeptide, has been introduced by means of recombinant DNA techniques. The progeny of such a cell are also considered within the scope of the invention.

The precise components of the expression system are not critical. For example, a mutant EGF polypeptide can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (*Cloning Vectors: A Laboratory Manual*, 1985 Suppl. 1987).

The expressed polypeptides can be purified from the expression system using routine biochemical procedures, and can be used, e.g., as therapeutic agents, as described herein.

Methods of Treatment

The mutant EGF polypeptides, and nucleic acids expressing them, can be administered to a cell to modulate EGFR activity in the cell. The cell can be a cell in a subject, and the polypeptides or nucleic acids can be administered in vivo or ex vivo. Mutant EGF polypeptides can bind to EGFR-expressing cells such as fibroblasts, endothelial cells, epithelial cells, and keratinocytes.

As used herein, the term "subject" is intended to include human and non-human animals. Preferred human animals include a human patient having a disorder characterized by abnormal cell proliferation or cell differentiation. The term "non-human animals" of the invention includes all vertebrates, e.g., non-mammals (such as chickens, amphibians, reptiles) and mammals, such as non-human primates, mice, sheep, dogs, cows, and pigs. In one embodiment, the subject is a human subject.

Cancers

The mutant EGF polypeptides and nucleic acids can be used to treat a subject at risk for, or having a disorder associated with cell growth or a differentiative process, for example, a cellular proliferative disorder or cellular differentiative disorders, for example, by modulating EGFR activity. Examples of cellular proliferative and/or differentiative disorders include cancer (e.g., carcinoma, sarcoma, metastatic disorders or hematopoietic neoplastic disorders including leukemias). A metastatic tumor can arise from a multitude of primary tumor types, including but not limited to those of prostate, colon, lung, breast and liver origin.

The mutant EGF polypeptides can be used to kill, ablate, or inhibit the growth of cancerous cells and normal, benign hyperplastic, and cancerous cells in vivo. The polypeptides can be used by themselves or conjugated to an agent, for example, a toxic moiety (e.g., a cytotoxic drug, a toxin, or a radioisotope). This method includes administering the ligand alone or attached to a toxic moiety to a subject requiring such treatment.

In one embodiment, a mutant EGF polypeptide is administered in combination with a second agent. Nonlimiting examples of agents which can be used in combination with a mutant EGF polypeptide in methods of treating cancers include, e.g., antimicrotubule agents (e.g., paclitaxel, taxotere), topoisomerase inhibitors (e.g., doxorubicin, etoposide), antimetabolites (e.g., 5-fluorouracil (5-FU), methotrexate, 6-mercaptopurine), mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates).

Mutant EGF polypeptides can also bind to cells in the vicinity of the cancerous cells. The mutants can inhibit the growth of, and/or kill these cells. In this manner, the ligands may indirectly attack the cancerous cells which may rely on surrounding cells for nutrients, growth signals and so forth.

Thus, the mutants (e.g., modified with a cytotoxin) can selectively target cells in cancerous tissue (including the cancerous cells themselves).

The mutants may be used to deliver a variety of cytotoxic drugs.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. Procedures for preparing enzymatically active polypeptides of the immunotoxins are described in W084/03508 and W085/03508. Examples of cytotoxic moieties that can be conjugated to the antibodies include adriamycin, chlorambucil, daunomycin, methotrexate, neocarzinostatin, and platinum.

In the case of polypeptide toxins, recombinant nucleic acid techniques can be used to construct a nucleic acid that encodes the mutant EGF polypeptide and the cytotoxin (or a polypeptide component thereof) as translational fusions. The recombinant nucleic acid is then expressed, e.g., in cells and the encoded fusion polypeptide isolated.

Procedures for conjugating protein ligands (e.g., antibodies) with the cytotoxic agents have been previously described. Methods for generating fusions of EGF with diphtheria toxin and techniques for delivering the polypeptides to a subject are described, e.g., in Cohen, et al., *Curr Pharm Biotechnol.* 4:39-49, 2003; and Shaw, et al., *J Biol Chem* 266:21118-21124, 1991. These fusions and methods of administration can be used, for example, in the treatment of glioblastoma multiforme.

Alternatively, the mutant EGF polypeptide can be coupled to high energy radiation emitters, for example, a radioisotope, such as $^{131}I$, a γ-emitter, which, when localized at the tumor site, results in a killing of several cell diameters. Other suitable radioisotopes include α-emitters, such as $^{212}Bi$, $^{213}Bi$, and $^{211}At$, and β-emitters, such as $^{186}Re$ and $^{90}Y$.

Also encompassed by the present invention is a method of killing or ablating which involves using the mutant EGF polypeptides for prophylaxis. For example, these materials can be used to prevent or delay development or progression of cancers.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof.

Wound and Injury Healing

The mutant EGF polypeptides and nucleic acids can be used to accelerate regeneration of damaged tissues. For example, mutant EGF polypeptides can be administered to subjects at risk for or having gastric or oral ulcers, foot ulcers (e.g., diabetes-associated), corneal epithelial wounds, epidermal lesions, tympanic membrane perforations, and other types of tissue lesions. Preferably, a mutant EGF polypeptide is used which agonizes EGFR, e.g., to stimulate cellular growth and differentiation processes involved in wound healing. Topical and intravenous administration of EGF to mucosal ulcers in mammals is described, e.g., in Fujisawa, et al., *J Oral Pathol Med* 32:358-366, 2003. In this study, rabbits were administered 1 µg/kg per day until the wounds healed. Topical use of EGF to stimulate healing of venous ulceration in humans is described, e.g., in Falanga et al., *J Dermatol Surg Oncol.* 18(7):604-6, 1992. In this study, 10 µg/mL of recombinant human EGF was applied topically to the ulcers twice a day until healing occurred or for ten weeks. Other methods of using EGF for treatment of wounds are described in Brown et al., *N Engl J Med.* 321(2):76-9, 1989 and Brown et al., *Plast Reconstr Surg.* 88(2):189-94, 1991.

Other Applications

The mutant EGF polypeptides described herein can be used in applications in which regulation of cell growth, differentiation, and activity is desired. This includes treatment of conditions in which cell growth is desirable, e.g., for regeneration of specific tissue types, and/or other conditions in which EGFR activity has a useful biological effect. For example, mutant EGF polypeptides may be used to stimulate repair of tympanic membrane perforations. See, e.g., Ma et al., *Acta Otolaryngol.* 122(6):586-99, 2002. Mutant EGF polypeptides can also be used to stimulate survival or regeneration of neurons (Xian et al., *Mol Neurobiol.* 20(2-3):157-83, 1999) and β-cells of the pancreas (Brand, et al., *Pharmacol Toxicol.* 91(6):414-20, 2002). Mutant EGF polypeptides can also be used in cosmetic compositions (U.S. Pat. No. 6,589,540).

Pharmaceutical Compositions and Methods of Administration

The mutant EGF polypeptides and nucleic acids can be incorporated into pharmaceutical compositions. Such compositions typically include the polypeptide or nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral (e.g., intravenous, intradermal, subcutaneous, transdermal (topical), transmucosal, and rectal administration). Parenteral administration is typical, however, the polypeptides described here may be formulated for oral administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide, e.g., to a pH of about 7.2-7.8, e.g., 7.5. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the mutant EGF polypeptides or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds (mutant EGF polypeptides or nucleic acids) can also be prepared in the form of suppositories (e.g., with conventional suppository bases such as cocoa butter and other glycerides) or retention enemas for rectal delivery.

The compounds (mutant EGF polypeptides or nucleic acids) can also be administered by transfection or infection using methods known in the art, including but not limited to the methods described in McCaffrey et al. *Nature,* 418(6893): 38-9, 2002, (hydrodynamic transfection); Xia et al. *Nature Biotechnol.,* 20(10):1006-10, 2002, (viral-mediated delivery); or Putnam, *Am. J. Health Syst. Pharm.* 53(2), 151-160, 1996, erratum at *Am. J. Health Syst. Pharm.* 53(3):325, 1996.

Additionally, intranasal delivery is possible, as described in, inter alia, Hamajima et al. *Clin. Immunol. Immunopathol.* 88(2):205-10, 1998, Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the mutant EGF polypeptides or nucleic acids are prepared with carriers that will protect the mutant EGF polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such mutant EGF polypeptides or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a mutant EGF polypeptides (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1 st International Standard for Interleukin-2 (human)). The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the mutant EGF polypeptides of the invention can include a single treatment or, can include a series of treatments. In one embodiment, the compositions are administered every 8 hours for five days, followed by a rest period of two to 14 days, for example, 9 days, followed by an additional five days of administration every 8 hours.

The pharmaceutical compositions can be included in a container, pack, or dispenser together with instructions for administration.

Also within the scope of the invention are kits comprising a mutant EGF polypeptide and instructions (e.g., a written and/or illustrated for therapeutic use. The kit can further contain a least one additional reagent, such as a label or additional therapeutic agent.

EXAMPLES

The invention is further described in the following examples, which do not limit the scope of the invention described in the claims.

Example 1

Production and Screening of EGF Mutants Using Yeast Surface Display

Mutagenic DNA was created by error prone PCR using nucleotide analogs. The human EGF gene was subcloned into the pCT302 backbone at NheI and BamHI restriction sites. This vector is termed pCT EGF. The yeast display construct includes a C-terminal c-myc epitope tag for detection and quantitation of cell surface proteins. PCR primers with 50 bp of overlapping sequence in the forward and reverse direction were designed for homologous recombination in yeast (Swers et al., *Nucleic Acids Res.*, 32:e36, 2004). Primers were truncated at the NheI (5') and BamHI (3') restriction sites flanking the EGF insert. The pCT EGF plasmid was subjected to random mutagenesis by error-prone PCR with low fidelity Taq polymerase (Invitrogen) and 50 mM $MgCl_2$. To tune the mutagenic frequency, varying amounts of the nucleotide analogs 8-oxo-dGTP (4 μM, 40 μM, or 400 μM) and dPTP (2 μM, 20 μM, or 200 μM) (TriLink Biotech) were used in separate PCR consisting of 5, 10 and/or 20 cycles (Zaccolo et al., *J. Mol. Biol.*, 255:589-603, 1996; Zaccolo and Gherardi, *J. Mol. Biol*, 285:775-783, 1999). PCR products were amplified in the absence of nucleotide analogs, and 90 μg of mutagenic DNA insert and 9 μg of restriction enzyme cut pCT vector backbone were transformed into EBY100 competent yeast cells (Boder and Wittrup, *Nat. Biotechnol.*, 15:553-557, 1997) by electroporation (Meilhoc et al., *Biotechnology*, 8:223-227, 1990). A library of ~1.2×107 yeast transformants was obtained, as estimated by plating aliquots of the library and colony counting. The library was propagated and induced for protein expression at 30° C. by the addition of galactose to the culture media.

A sampling of clones from the original library demonstrated a range of mutation frequencies from 1 to 14 amino acid changes in the EGF protein. Soluble EGFR extracellular domain produced in insect cells was fluorescently labeled and used to screen the mutant EGF library displayed on the surface of yeast. Flow cytometric sorting was used to isolate several EGF mutants that exhibited enhanced binding to soluble EGFR.

For screening by flow cytometry, $10^8$ induced yeast cells were labeled with 200 nM of Alexa-488 labeled EGFR for 2 h at 37° C. in phosphate-buffered saline containing 1 mg/ml BSA (FACS buffer). To detect expression of the C-terminal c-myc epitope tag, a 1:10 dilution of monoclonal antibody 9E10 (Covance) was added for the last 30 min of incubation. Yeast cells were washed with ice-cold FACS buffer and labeled with a 1:6 dilution of goat anti-mouse phycoerythrin secondary antibody (Sigma) for 15 min at 4° C. Cells were washed and screened by dual-color flow cytometric sorting for yeast cells which both displayed EGF mutant proteins and bound to Alexa-488 EGFR using a DakoCytomation (Carpinteria, Calif.) MoFlo FACS machine. Collected yeast cells were cultured, induced for expression, and subjected to two subsequent rounds of flow cytometric sorting with 50 nM of Alexa-488 EGFR. Plasmid DNA was recovered from yeast clones isolated after the second and third sorts using a Zymoprep[198] kit (Zymo Research) and amplified in XL1-blue supercompetent *Escherichia coli* cells (Stratagene).

The amino acid sequences of these EGF mutants identified in this screen are listed in Table I (FIG. 1). Interestingly, it was noticed that many of the EGF mutations that contributed to enhanced receptor binding were homologous substitutions that were present in other EGF species (FIG. 3) and generally occur in non-conserved regions of the protein. Table IV, below, lists the nucleotide sequences of mutations occurring three times or more in mutants identified in this screen.

Example 2

Binding of EGF Mutants to EGFR

EGF mutants isolated from the library screens were expressed on the surface of yeast and treated with 50 nM soluble Alexa-EGFR for 2 hr at 37° C. Fluorescence intensity of cell surface labeling was measured by flow cytometry (FIG. 5).

Figure 6:
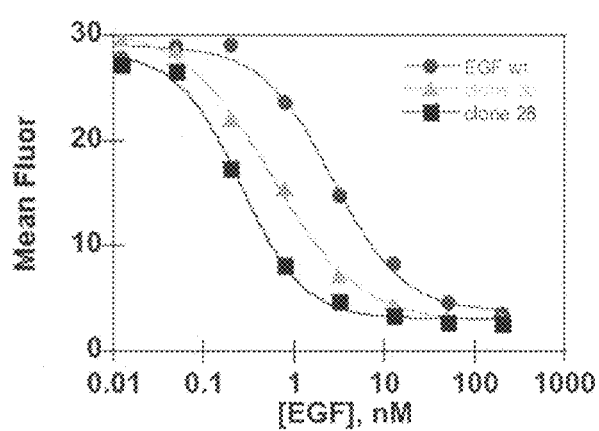
FIG. 6 is a line graph generated from binding studies of wild-type EGF and EGF mutants (clones 28 and 30) to NR6 fibroblast cells. Wt and mutant EGF binding to EGFR on NR6 fibroblast cells was measured by a competition binding assay. Increasing concentrations of unlabeled EGF were mixed with a constant amount of labeled wt EGF and incubated with fibroblast cells. Fluorescence intensity of cell surface labeling was measured by flow cytometry.

Two of the EGF mutants, clone 28 and clone 30 were produced solubly and were tested for binding to fibroblast cells expressing EGFR. Binding of wt EGF, clone 28, and clone 30 to EGFR on NR6 fibroblast cells was measured by a competition binding assay (FIG. 6). Increasing concentrations of unlabeled EGF were mixed with a constant amount of Alexa-488 labeled wt EGF and incubated with fibroblast cells for 2 hr at 4° C. Fluorescence intensity of cell surface labeling was measured by flow cytometry. Dissociation constants at half-maximal values were: 2.7±0.4 nM (wt), 0.56±0.07 nM (clone 30), and 0.26±0.03 nM (clone 28). Thus, clone 28 and clone 30 exhibited a 5 to 10-fold increase in affinity over wt EGF.

Example 3

Biological Activity of EGF Mutant Clone 28

Figure 7:
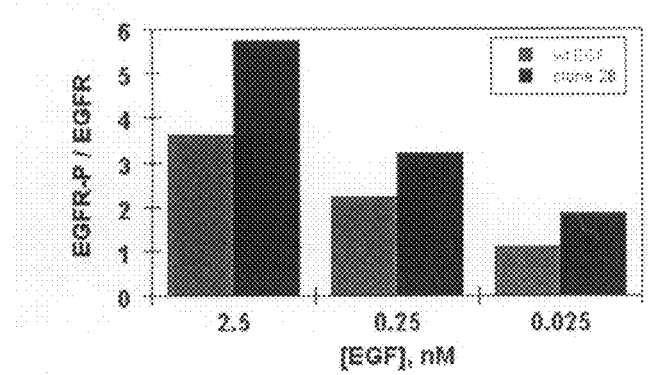
FIG. 7 is a bar graph demonstrating that EGF mutant clone 28 enhances EGF receptor phosphorylation. Soluble EGF wt and mutant clone 28 were added to NR6 fibroblast cells at the indicated concentrations. Phosphorylation of EGFR in the presence of these proteins was analyzed by Western blotting and quantitated. Data shown are the ratio of phosphorylated EGFR/total EGFR.

EGFR phosphorylation in the presence of wt EGF and mutant clone 28 was evaluated. Soluble EGF wt and mutant clone 28 were added to NR6 fibroblast cells at the concentrations indicated in FIG. 7 for 1 min at 37° C. Cells were lysed and levels of Tyr1173 phospho-EGFR were measured by Western blot, probing with a phospho-specific rabbit polyclonal antibody (Santa Cruz Biotech). Blots were stripped and reprobed with rabbit polyclonal EGFR to determine the total amount of EGFR protein present. Westerns were developed using enhanced chemiluminescence, and band density of was quantitated using a Bio-Rad Fluor-S Imager. Data shown is the ratio of phosphorylated EGFR/total EGFR. The data on EGF mutant clone 28 demonstrate that this mutant increases receptor phosphorylation on fibroblast cells (FIG. 7).

Example 4

Production and Screening of Second Generation EGF Mutants Using Yeast Surface Display A second generation EGF library was created by shuffling the original mutagenic DNA with enriched pools from the first round of sorting. In addition to DNA shuffling, a library was made by doping oligonucleotide sequences corresponding to variable amino acid residues found in EGF family members.

The additional EGF mutant libraries were constructed as follows. DNA templates from the original error prone PCR (45%), the enriched library pool from the first round of EGF affinity maturation (45%), and single clones of affinity enhanced EGF mutants (1% each of 10 mutants) were randomly fragmented with DNase I for 7 min at 15° C. DNA fragments were purified using a Qiaex II kit (Qiagen), reannealed, and amplified by PCR with primers as described above for homologous recombination. 112 µg of shuffled, mutagenic DNA and 5.4 µg of restriction enzyme cut acceptor vector was transformed into the yeast strain EBY100 by homologous recombination to create a library of ~$10^7$ clones. For shotgun orthologous scanning mutagenesis (SOSM), DNA templates from error-prone PCR (percentages as described above) were shuffled with single-stranded oligonucleotides that were ~25 bases in length and corresponded to orthologous mutations. Seven separate self assembly reactions were performed combining two or three oligonucleotides (500 ng of each) and 0.8 mg of DNase I treated fragments, such that their DNA sequences did not overlap. One additional doping reaction was set up combining all 19 oligonucleotide sequences (2 µg total) with 1 mg of DNase treated fragments. Re-assembled DNA was amplified by PCR as above, and 15 µg of each insert (120 µg total) was transformed with 0.65 µg of cut acceptor vector (5.2 mg total) into yeast by homologous recombination to create a library of ~$7\times10^6$ clones.

These libraries were transformed into yeast and screened for increased binding to soluble EGFR ECD by flow cytometry. Clones were isolated from these new libraries with increased EGFR binding affinities over the first generation EGF mutants. The amino acid sequences of these mutants are listed in Table II (FIG. 2A) and Table III (FIG. 2B). Table V, below, lists the nucleotide sequences of mutations occurring three times or more in mutants identified in this screen.

Example 5

Binding of Second Generation EGF Mutants to EGFR

Figure 8:
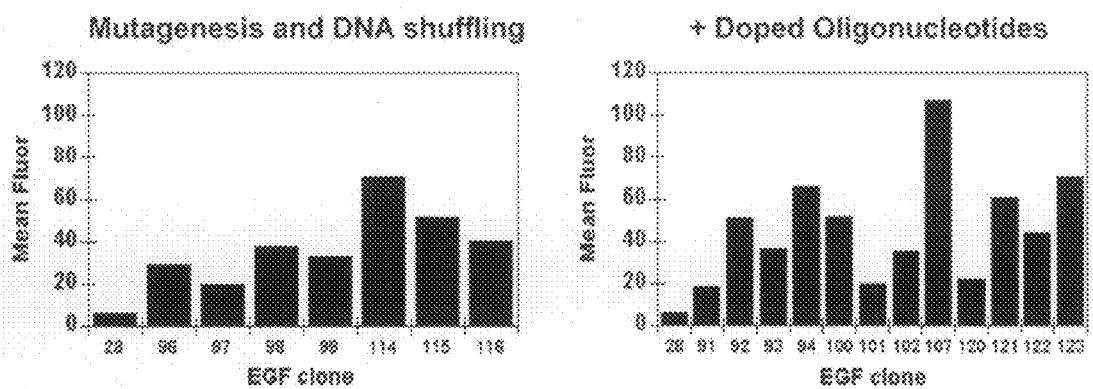
FIG. 8 is a pair of bar graphs generated by binding studies with second generation EGF mutants (clones 96, 97, 98, 99, 114, 115, 116, 91, 92, 93, 94, 100, 101, 102, 107, 120, 121, 122, and 123). Binding of second generation EGF mutants displayed on yeast to soluble EGFR. Second generation EGF mutants isolated from the library screens were expressed on the surface of yeast and treated with soluble fluorescent EGFR. Fluorescence intensity of cell surface labeling was measured by flow cytometry. EGF clone 28, isolated from the first generation mutant library, is included for comparison. The graph on the left-hand side represents studies with mutants produced by mutagenesis and DNA shuffling. The graph on the right-hand side represents mutants produced by mutagenesis, DNA shuffling, and oligo doping.

Mutants from these libraries exhibit a ~20-fold increase in binding affinity to fibroblast cells over wt EGF. Binding of these clones to EGFR is depicted in FIG. 8. To evaluate binding, these clones were expressed on the surface of yeast and treated with 1.2 nM soluble Alexa-EGFR for 1.5 hr at 37° C. Fluorescence intensity of cell surface labeling was measured by flow cytometry. EGF clone 28, isolated from the first generation mutant library, is included for comparison.

Figure 9:
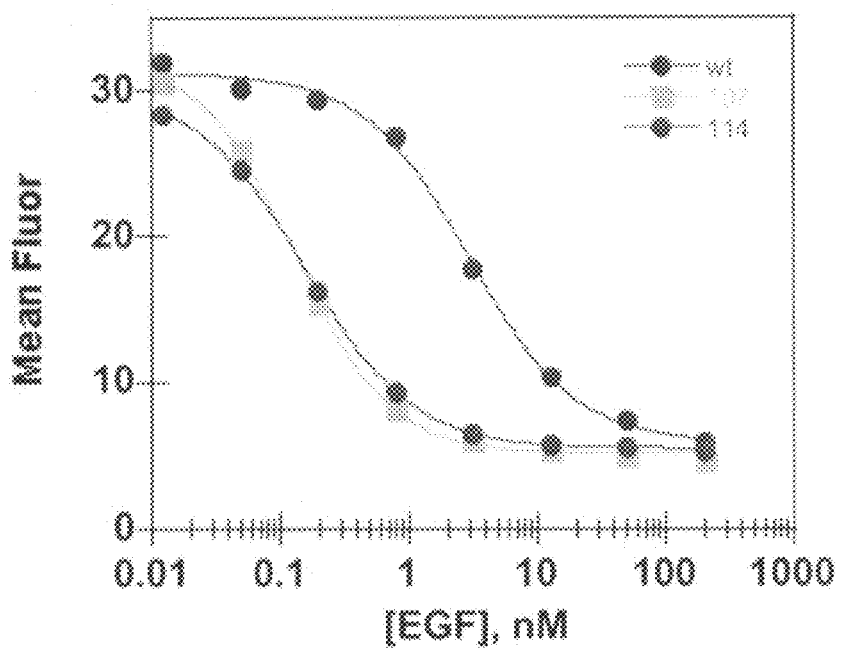
FIG. 9 is a line graph generated from binding studies of wild-type and second generation mutants. Second generation EGF mutants bind with high affinity to NR6 fibroblasts. The binding of soluble EGF wt and mutants to NR6 fibroblast cells was measured by a competition assay. Increasing concentrations of unlabeled EGF were mixed with a constant amount of EGF. Fluorescence intensity of cell surface labeling was measured by flow cytometry.
Figure 10:
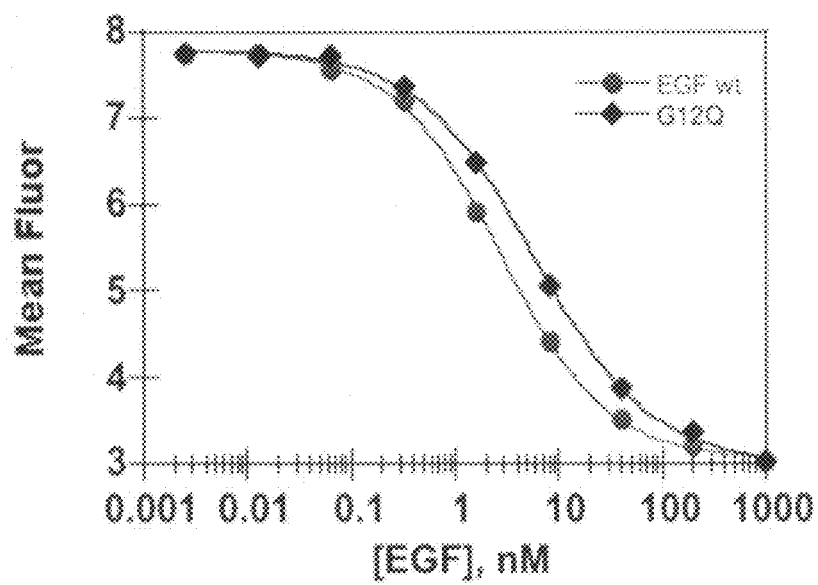
FIG. 10 is a line graph generated from binding studies of yeast engineer EGF mutants. Yeast engineered EGF mutants have a higher receptor binding affinity than EGF G12Q. The binding of soluble wtEGF and G12Q to NR6 fibroblast cells was measured by a competition assay. Increasing concentrations of unlabeled EGF were mixed with a constant amount of wt EGF and incubated with fibroblast cells. Fluorescence intensity of cell surface labeling was measured by flow cytometry.

Two of the second generation EGF mutants, clone 107 and clone 114 were produced solubly and were tested for binding to fibroblast cells expressing EGFR by a competition assay (FIG. 9). Increasing concentrations of unlabeled EGF were mixed with a constant amount of Alexa-488 labeled wt EGF and incubated with fibroblast cells for 6 hr at 4° C. Fluorescence intensity of cell surface labeling was measured by flow cytometry. Equilibrium dissociation constants were determined to be 2.9±0.34 (wt), 0.16±0.01 (clone 114), and 0.13±0.01 (clone 107). clones 121 and 123, isolated from SOSM, competed for binding to the fibroblast cells with an $IC_{50}$ of 0.14±0.07 nM and 0.49±0.25 nM, respectively.

Example 6

Binding Activity of a Previously Described EGF Mutant

EGF containing a G12Q mutation was reported to have a five-fold increase in binding and activation over wt EGF (Mullenbach, et al., *Protein Eng* 11:473-480, 1998).

This mutant was tested using one of the binding assays described herein in which binding to EGFR expressed on cells is measured. The binding of soluble wt EGF and G12Q to NR6 fibroblast cells was measured by a competition assay. Increasing concentrations of unlabeled EGF were mixed with a constant amount of Alexa-488 labeled wt EGF and incubated with fibroblast cells for 2 hr at 4° C. Fluorescence intensity of cell surface labeling was measured by flow cytometry. Equilibrium dissociation constants were determined to be 2.8±0.15 (wt) and 5.7±0.39 (G12Q). This result contradicts previous data that EGF G12Q exhibits a 5-fold increase in affinity for EGFR (Mullenbach, et al., *Protein Eng* 11:473-480, 1998).

TABLE IV

Nucleotide sequences of 3X mutations isolated by separate error-prone PCR and DNA shuffled libraries

| | N1S | S2R | D3G | E5G | L8P | H10Y | H16Q | D17G | E24K | E24G | K28R | I38A | I38T | K48T | K48R |
|---|---|---|---|---|---|---|---|---|---|---|---|---|---|---|---|
| Library 1: Nucleotide analog mutagenesis | | | | | | | | | | | | | | | |
| Wt | AAT | AGT | GAC | GAA | CTG | CAC | CAT | GAT | GAA | GAA | AAG | ATC | ATC | AAG | AAG |
| 27 | | | GGA | | | | | | | | | | ACC | | AGG |
| 28 | | | | | | | | GGT | AAA | | AGG | | | ACG | |
| 29 | | | | | | | | | AAG | | | GCC | | | AGG |
| 30 | AGT | | GGA | | | | | | | | AGG | GCC | | | |
| 31 | | | | | | | | | | | | | | | AGG |
| 33 | | GGC | | | | | | | | | | | | | AGG |
| 34 | | | | | | | | | | | | | | | AGG |
| 35 | | | | | TAC | | | | | | | | | | |
| 43 | | | | | | | | | | | AGG | | | | AGG |
| 45 | | | | | | | | | AAA | | | | ACC | | AGG |
| 46 | | | | | | | | | | | | GCC | | | AGG |
| 51 | | GGC | | | | | | | | | GGA | AGG | | | AGG |
| Library 2: Mutagenesis and DNA shuffling | | | | | | | | | | | | | | | |
| 96 | | GGC | GGA | CCG | TAC | CAG | GGT | | GGA | AGG | | | | | |
| 97 | | | | | | | | | AAG | | | | ACC | | AGG |
| 99 | | | | | | | | | | | | GCC | | | AGG |
| 103 | | | | | | | | | | | AGG | | | | AGG |
| 114 | AGT | AGG | GGC | | CCG | | CAG | GGT | | | AGG | GCC | | ACG | |
| 115 | | | GGA | | | | | | AAA | | AGG | GCC | | | AGG |
| 116 | AGT | | GGC | | CCG | | | GGT | | | | | ACC | | AGG |
| 130 | | | | | CCG | CAG | GGT | | | | AGG | | | ACG | |
| 131 | | AGG | GGC | | | | | | | | GGA | AGG | | ACC | AGG |
| 133 | | | GGA | | TAC | | | | AAA | | | GCC | | | AGG |
| 134 | AGT | AGG | GGC | | CCG | | | | | | AGG | GCC | | | AGG |

Nucleotide sequences of mutations occurring 3 times or more are indicated.

TABLE V

Nucleotide sequences of 3X mutations isolated from the SOSM library

| | N1S | D3G | D3Y | D3N | L8P | H10Y | H16N | M21R | K28R | I38A | I38V | K48R | E51G | E51A | L52R |
|---|---|---|---|---|---|---|---|---|---|---|---|---|---|---|---|
| Wt | AAT | GAC | GAC | GAC | CTG | CAC | CAT | ATG | AAG | ATC | ATC | AAG | GAA | GAA | CTG |
| SOSM[a] | | | TAC | AAT | CCT | TAC | AAT | | CGT | | GTT | CGT | | | |

TABLE V-continued

Nucleotide sequences of 3X mutations isolated from the SOSM library

| | N1S | D3G | D3Y | D3N | L8P | H10Y | H16N | M21R | K28R | I38A | I38V | K48R | E51G | E51A | L52R |
|---|---|---|---|---|---|---|---|---|---|---|---|---|---|---|---|
| 91 | AGT | GGC | | | | | | | CGT | GCC | | AGG | GGA | | CGG |
| 92 | AGT | | AAC | CCT | | | | | AGG | GCC | | AGG | | GCA | CGG |
| 93 | | TAC | | | | | CGG | | | | | AGG | GGA | | |
| 94 | | GGC | | | | TAC | | | AGG | | | | | | |
| 100 | | | AAT | | | AAT | AGG | | | | GTC | AGG | | | |
| 101 | | GGC | | | TAC | AAT | | | | | | AGG | | | |
| 102 | | | AAT | | | AAT | | | | | GTT | | GGA | | |
| 107 | | TAC | | TAC | AAT | AGG | AGG | | | | | | | | |
| 120 | AGT | GGC | | | CCG | | AAT | | | | | | | | |
| 121 | | | | | | AAT | | AGG | | | GTT | | | GCA | |
| 122 | | AAT | | | AAT | | | AGG | GCC | | | AGG | GGA | | |
| 123 | | TAC | CCG | TAC | | AGG | | | GCC | | | AGG | GGA | | CGG |
| 124 | | AAT | | | AAT | | AGG | | | GTT | AGG | GGA | | | |
| 129 | AGT | GGC | | | AAT | | | | | GTT | AGG | | | GCA | CGG |

Nucleotide sequences of mutations occurring 3 times or more are indicated.
$^a$indicates doped oligonucleotide sequences.

A number of embodiments of the invention have been described. Nevertheless, it will be understood that various modifications may be made without departing from the spirit and scope of the invention. Accordingly, other embodiments are within the scope of the following claims.

---

What is claimed is:

1. An isolated polypeptide comprising the sequence of a mutant epidermal growth factor (EGF) that conforms to the amino acid sequence $X_1$-$X_2$-$X_3$-$X_4$-$X_5$-C-P-$X_8$-$X_9$-$X_{10}$-$X_{11}$-G-$X_{13}$-C-L-$X_{16}$-$X_{17}$-G-$X_{19}$-C-$X_{21}$-Y-I-$X_{25}$-$X_{26}$-D-$X_{28}$-Y-$X_{30}$-C-$X_{32}$-C-$X_{34}$-$X_{35}$-G-Y-$X_{38}$-G-E-R-C-Q-Y-$X_{45}$-$X_{46}$-L-$X_{48}$-$X_{49}$-$X_{50}$-$X_{51}$-$X_{52}$-$X_{53}$ (SEQ ID NO:47), wherein X represents any amino acid residue except cysteine (C); the sequence of the mutant EGF differs from SEQ ID NO:1 (wild type EGF) by including 3-10 amino acid substitutions; and the mutant EGF comprises amino acid substitutions at $X_{48}$, $X_{51}$, and $X_{52}$.

2. The isolated polypeptide of claim 1, wherein the mutant EGF comprises 3, 4, 5, 6, 7, or 8 amino acid substitutions.

3. The isolated polypeptide of claim 1, wherein $X_{48}$ is R or T.

4. The isolated polypeptide of claim 1, wherein $X_{51}$ is G, A, W, K, or Y.

5. The isolated polypeptide of claim 1, wherein $X_{52}$ is P, R, or T.

6. The isolated polypeptide of claim 1, wherein the mutant EGF consists of SEQ ID NO:3, SEQ ID NO:15, SEQ ID NO:17, SEQ ID NO:19, SEQ ID NO:22, SEQ ID NO:23, SEQ ID NO:24, SEQ ID NO:25, SEQ ID NO:26, SEQ ID NO:36, or SEQ ID NO:38.

7. The isolated polypeptide of claim 1, wherein the polypeptide consists of the mutant EGF.

8. The isolated polypeptide of claim 6, wherein the polypeptide consists of the mutant EGF.

9. The isolated polypeptide of claim 1, wherein the mutant EGF binds a human EGF receptor.

10. The isolated polypeptide of claim 6, wherein the mutant EGF binds a human EGF receptor with at least five-fold higher affinity than SEQ ID NO:1 (wild type EGF) binds the EGF receptor.

11. A kit comprising: a polypeptide of claim 1 and instructions for diagnostic or therapeutic use.

* * * * *

UNITED STATES PATENT AND TRADEMARK OFFICE
CERTIFICATE OF CORRECTION

PATENT NO.        : 8,247,531 B2          Page 1 of 1
APPLICATION NO.   : 11/725695
DATED             : August 21, 2012
INVENTOR(S)       : Jennifer R. Cochran et al.

It is certified that error appears in the above-identified patent and that said Letters Patent is hereby corrected as shown below:

In the Specification

Please amend the paragraph beginning col. 1, line 8, of the application as originally filed (the paragraph under the heading "Federally Sponsored Research or Development") as follows:

This invention was made with government support under grant numbers BRP CA096504 and F32 CA94796-01, awarded by the National Institutes of Health. The government has certain rights in the invention.

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,247,531 B2 |
| APPLICATION NO. | : 11/725695 |
| DATED | : August 21, 2012 |
| INVENTOR(S) | : Jennifer R. Cochran et al. |

It is certified that error appears in the above-identified patent and that said Letters Patent is hereby corrected as shown below:

In the Specification

Column 1 line 8 should read

"This invention was made with Government support under Grant Nos. F32 CA094796 and R01 CA096504 awarded by the National Institutes Of Health. The Government has certain rights in the invention."

Signed and Sealed this
Seventh Day of June, 2016

Michelle K. Lee
*Director of the United States Patent and Trademark Office*

SEQUENCE LISTING

<160> NUMBER OF SEQ ID NOS: 49

<210> SEQ ID NO 1
<211> LENGTH: 53
<212> TYPE: PRT
<213> ORGANISM: Homo sapiens

<400> SEQUENCE: 1

Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 2

```
Asn Ser Asp Ser Gly Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Thr Gly Glu Arg Cys Gln Tyr Arg Asp Leu Arg
                35                  40                  45

Trp Trp Glu Leu Arg
        50

<210> SEQ ID NO 3
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 3

Asn Ser Asp Ser Glu Cys Pro Leu Ser His Asp Gly Tyr Cys Leu His
 1               5                  10                  15

Gly Gly Val Cys Met Tyr Ile Lys Ala Val Asp Arg Tyr Ala Cys Asn
            20                  25                  30

Cys Val Val Gly Tyr Ile Gly Glu Arg Cys Gln Tyr Arg Asp Leu Thr
                35                  40                  45

Trp Trp Gly Pro Arg
        50

<210> SEQ ID NO 4
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 4

Asn Ser Asp Ser Glu Cys Pro Leu Ser His Asp Gly Tyr Cys Leu His
 1               5                  10                  15

Asp Gly Val Cys Val Tyr Ile Lys Thr Leu Asp Lys Tyr Ala Cys Asn
            20                  25                  30

Cys Val Val Gly Tyr Ala Gly Glu Arg Cys Gln Tyr Arg Asp Leu Arg
                35                  40                  45

Trp Trp Glu Leu Arg
        50

<210> SEQ ID NO 5
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 5

Ser Ser Asn Ser Gly Cys Pro Leu Ser His Asp Gly Tyr Cys Leu His
 1               5                  10                  15

Asp Gly Val Cys Met Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Lys
                35                  40                  45

Trp Trp Glu Leu Arg
        50
```

```
<210> SEQ ID NO 6
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 6

Asn Ser Asp Ser Glu Cys Pro Leu Ser His Asp Gly Tyr Cys Leu His
 1               5                  10                  15

Asp Gly Ala Cys Val Tyr Ile Glu Ala Leu Asp Lys Tyr Ala Cys Asn
            20                  25                  30

Cys Val Val Gly Tyr Val Gly Glu Arg Cys Gln Tyr Arg Asp Leu Arg
        35                  40                  45

Trp Trp Gly Arg Arg
    50

<210> SEQ ID NO 7
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 7

Asn Ser Gly Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Arg
        35                  40                  45

Trp Trp Glu Leu Arg
    50

<210> SEQ ID NO 8
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 8

Asn Ser Asp Ser Glu Cys Pro Leu Ser His Asp Gly Tyr Cys Leu His
 1               5                  10                  15

Asp Gly Ala Cys Met Tyr Ile Glu Ala Leu Asp Lys Tyr Val Cys Asn
            20                  25                  30

Cys Ala Val Gly Tyr Ile Gly Glu Arg Cys Gln Tyr Arg Asp Leu Arg
        35                  40                  45

Trp Trp Gly Pro Arg
    50

<210> SEQ ID NO 9
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 9

Asn Gly Asp Ser Glu Cys Pro Leu Ser Tyr Asp Gly Tyr Cys Leu His
 1               5                  10                  15

Asp Gly Val Cys Met Tyr Ile Glu Ala Leu Asp Lys Tyr Ala Cys Asn
            20                  25                  30
```

```
Cys Val Val Gly Tyr Ile Gly Glu Arg Cys Gln Tyr Arg Asp Leu Lys
            35                  40                  45

Trp Trp Glu Arg Arg
     50
```

<210> SEQ ID NO 10
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 10

```
Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Arg Tyr Ala Cys Asn
             20                  25                  30

Cys Val Val Gly Tyr Ile Gly Glu Arg Cys Gln Tyr Arg Asp Leu Arg
            35                  40                  45

Trp Trp Glu Leu Arg
     50
```

<210> SEQ ID NO 11
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 11

```
Asn Ser Asp Ser Glu Cys Pro Leu Ser His Asn Gly Tyr Cys Leu His
 1               5                  10                  15

Asp Gly Val Cys Met Tyr Ile Lys Ala Leu Asp Lys Tyr Ala Cys Asn
             20                  25                  30

Cys Val Ala Gly Tyr Thr Gly Glu Arg Cys Gln Tyr Arg Asp Leu Arg
            35                  40                  45

Trp Trp Gly Leu Arg
     50
```

<210> SEQ ID NO 12
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 12

```
Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
             20                  25                  30

Cys Val Val Gly Tyr Ala Gly Glu Arg Cys Gln Tyr Arg Asp Leu Arg
            35                  40                  45

Trp Trp Ala Arg Arg
     50
```

<210> SEQ ID NO 13
<211> LENGTH: 53
<212> TYPE: PRT
<213> ORGANISM: Artificial Sequence
<220> FEATURE:
<223> OTHER INFORMATION: Mutant of human epidermal growth factor

```
<400> SEQUENCE: 13

Asn Ser Gly Ser Lys Cys Pro Leu Ser His Asp Gly Tyr Cys Leu His
1               5                   10                  15

Asp Gly Val Cys Met Tyr Ile Gly Ala Leu Asp Arg Tyr Ala Cys Asn
            20                  25                  30

Cys Val Val Gly Tyr Val Gly Glu Arg Cys Gln Tyr Arg Asp Leu Arg
        35                  40                  45

Trp Trp Glu Leu Arg
    50

<210> SEQ ID NO 14
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 14

Lys Ser Gly Pro Gly Cys Pro Pro Tyr Asp Gly Tyr Cys Leu Gln
1               5                   10                  15

Gly Gly Val Cys Met Tyr Ile Gly Ala Leu Asp Arg Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Pro Arg
    50

<210> SEQ ID NO 15
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 15

Asn Ser Asp Ser Glu Cys Pro Leu Ser His Asp Gly Tyr Cys Leu His
1               5                   10                  15

Asp Gly Val Cys Met Tyr Ile Lys Ala Leu Asp Lys Tyr Ala Cys Asn
            20                  25                  30

Cys Val Val Gly Tyr Thr Gly Glu Arg Cys Gln Tyr Arg Asp Leu Arg
        35                  40                  45

Trp Trp Gly Arg Arg
    50

<210> SEQ ID NO 16
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 16

Tyr Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ala Gly Glu Arg Cys Gln Tyr Arg Asp Leu Arg
        35                  40                  45

Trp Trp Glu Leu Arg
    50
```

<210> SEQ ID NO 17
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 17

Asn Ser Asn Ser Glu Cys Pro Leu Ser His Asp Gly Tyr Cys Leu His
1               5                   10                  15

Asp Gly Val Cys Arg Tyr Ile Glu Ala Leu Asp Arg Tyr Ala Cys Asn
            20                  25                  30

Cys Val Val Gly Tyr Ile Gly Glu Arg Cys Gln Tyr Gly Asp Leu Arg
        35                  40                  45

Trp Trp Gly Arg Arg
        50

<210> SEQ ID NO 18
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 18

Ser Arg Gly Ser Lys Cys Pro Pro Ser His Asp Gly Tyr Cys Leu Gln
1               5                   10                  15

Gly Gly Val Cys Met Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Thr
        35                  40                  45

Trp Trp Gly Arg Arg
        50

<210> SEQ ID NO 19
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 19

Asn Ser Asp Ser Gly Cys Pro Leu Ser His Ser Gly Tyr Cys Leu His
1               5                   10                  15

Asp Gly Val Cys Met Tyr Ile Lys Ala Leu Asp Arg Tyr Ala Cys Asn
            20                  25                  30

Cys Val Val Gly Tyr Ala Gly Glu Arg Cys Gln Tyr Arg Asp Leu Arg
        35                  40                  45

Trp Trp Ala Arg Arg
        50

<210> SEQ ID NO 20
<211> LENGTH: 51
<212> TYPE: PRT
<213> ORGANISM: Artificial Sequence
<220> FEATURE:
<223> OTHER INFORMATION: Mutant of human epidermal growth factor

<400> SEQUENCE: 20

Ser Ser Gly Ser Pro Pro Ser His Asp Gly His Cys Leu His Gly Gly
1               5                   10                  15

Val Cys Met Tyr Ile Glu Ala Leu Asp Lys Tyr Ala Cys Ser Cys Ala
            20                  25                  30

Val Gly Tyr Thr Gly Glu Arg Cys Gln Tyr Arg Gly Leu Arg Trp Trp
        35                  40                  45

Gly Leu Arg
    50

<210> SEQ ID NO 21
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 21

Asn Ser Asp Ser Glu Cys Pro Pro Ser His Asp Gly Tyr Cys Leu Gln
1               5                   10                  15

Gly Gly Val Cys Met Tyr Ile Glu Ala Leu Asp Arg Tyr Ala Cys Asn
            20                  25                  30

Cys Val Val Gly Tyr Ile Gly Glu Arg Cys Gln Tyr Arg Asp Leu Thr
        35                  40                  45

Trp Trp Glu Pro Arg
    50

<210> SEQ ID NO 22
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 22

Thr Arg Gly Ser Glu Cys Pro Leu Ser His Asp Gly Tyr Cys Leu His
1               5                   10                  15

Asp Gly Val Cys Met Tyr Ile Gly Ala Leu Asp Arg Tyr Ala Cys Asn
            20                  25                  30

Cys Val Val Gly Tyr Thr Gly Glu Arg Cys Gln Tyr Arg Asp Leu Arg
        35                  40                  45

Trp Trp Ala Arg Arg
    50

<210> SEQ ID NO 23
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 23

Asn Ser Asp Phe Gly Cys Pro Leu Ser Tyr Asp Gly Tyr Cys Leu His
1               5                   10                  15

Asp Gly Val Cys Met Tyr Ile Lys Ala Leu Asp Lys Tyr Ala Cys Asn
            20                  25                  30

Cys Val Val Gly Tyr Ala Gly Glu Arg Cys Gln Tyr Arg Asp Leu Arg
        35                  40                  45

Trp Trp Gly Arg Arg
    50

<210> SEQ ID NO 24
<211> LENGTH: 53
<212> TYPE: PRT
<213> ORGANISM: Artificial Sequence

```
<220> FEATURE:
<223> OTHER INFORMATION: Mutant of human epidermal growth factor

<400> SEQUENCE: 24

Ser Arg Gly Ser Lys Cys Pro Pro Ser His Asp Gly Tyr Cys Leu His
1               5                   10                  15

Asp Gly Val Cys Met Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Arg
        35                  40                  45

Trp Trp Ala Arg Arg
    50

<210> SEQ ID NO 25
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 25

Ser Ser Gly Ser Glu Cys Pro Ser Ser His Asp Gly Tyr Cys Leu His
1               5                   10                  15

Asp Gly Ala Cys Met Tyr Ile Glu Ala Leu Asp Arg Tyr Ala Cys Asn
            20                  25                  30

Cys Ala Val Gly Tyr Ala Gly Glu Arg Cys Gln Tyr Arg Asp Leu Arg
        35                  40                  45

Trp Trp Gly Arg Arg
    50

<210> SEQ ID NO 26
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 26

Ser Ser Asn Ser Glu Cys Pro Pro Ser His Asp Gly Tyr Cys Leu His
1               5                   10                  15

Asp Gly Val Cys Met Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Arg
        35                  40                  45

Trp Trp Ala Arg Arg
    50

<210> SEQ ID NO 27
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 27

Asn Ser Tyr Ser Glu Cys Pro Leu Ser His Asp Gly Tyr Cys Leu His
1               5                   10                  15

Gly Gly Val Cys Arg Tyr Ile Glu Ala Leu Asp Lys Tyr Ala Cys Asn
            20                  25                  30

Cys Val Val Gly Tyr Ser Gly Glu Arg Cys Gln Tyr Arg Asp Leu Arg
        35                  40                  45
```

Trp Trp Gly Leu Arg
    50

<210> SEQ ID NO 28
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 28

Asn Ser Gly Ser Glu Cys Pro Leu Ser Tyr Asp Gly Tyr Cys Leu His
1               5                   10                  15

Gly Gly Val Cys Met Tyr Ile Glu Ala Leu Asp Arg Tyr Ala Cys Asn
            20                  25                  30

Cys Val Val Gly Tyr Asn Gly Glu Arg Cys Gln Tyr Arg Asp Leu Lys
        35                  40                  45

Trp Trp Trp Leu Arg
    50

<210> SEQ ID NO 29
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 29

Asn Ser Asn Ser Glu Cys Pro Leu Ser His Asp Gly Tyr Cys Leu Asn
1               5                   10                  15

Asp Gly Val Cys Arg Tyr Ile Glu Ala Leu Asp Lys Tyr Ala Cys Asn
            20                  25                  30

Cys Val Val Gly Tyr Val Gly Glu Arg Cys Gln Tyr Arg Asp Leu Arg
        35                  40                  45

Arg Trp Glu Leu Arg
    50

<210> SEQ ID NO 30
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 30

Asn Ser Gly Ser Glu Cys Pro Leu Ser Tyr Asp Gly Tyr Cys Leu Asn
1               5                   10                  15

Asp Gly Val Cys Met Tyr Ile Gly Ala Leu Asp Lys Tyr Ala Cys Asn
            20                  25                  30

Cys Val Val Gly Tyr Thr Gly Glu Arg Cys Gln Tyr Gln Asp Leu Arg
        35                  40                  45

Trp Trp Lys Leu Arg
    50

<210> SEQ ID NO 31
<211> LENGTH: 53
<212> TYPE: PRT
<213> ORGANISM: Artificial Sequence
<220> FEATURE:
<223> OTHER INFORMATION: Mutant of human epidermal growth factor

<400> SEQUENCE: 31

His Ser Asn Ser Glu Cys Pro Leu Ser His Asp Gly Tyr Cys Leu Asn

```
                1               5                  10                  15
Asp Gly Val Cys Met Tyr Ile Lys Ala Leu Asp Thr Tyr Ala Cys Asn
                20                  25                  30

Cys Val Val Gly Tyr Val Gly Glu Arg Cys Gln Tyr Pro Asp Leu Lys
            35                  40                  45

Trp Trp Gly Leu Arg
        50

<210> SEQ ID NO 32
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 32

Asn Ser Tyr Ser Glu Cys Pro Leu Ser Tyr Asp Gly Tyr Cys Leu Asn
  1               5                  10                  15

Asp Gly Val Cys Arg Tyr Ile Glu Ala Leu Asp Arg Tyr Ala Cys Asn
                20                  25                  30

Cys Val Val Gly Tyr Ile Gly Glu Arg Cys Gln Tyr Arg Asp Leu Lys
            35                  40                  45

Trp Trp Trp Leu Arg
        50

<210> SEQ ID NO 33
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 33

Ser Arg Gly Ser Lys Cys Pro Pro Ser His Asp Gly Tyr Cys Leu Asn
  1               5                  10                  15

Asp Gly Val Cys Met Tyr Ile Glu Ala Leu Asp Lys Tyr Ala Cys Asn
                20                  25                  30

Cys Val Val Gly Tyr Leu Gly Glu Arg Cys Gln Tyr Arg Asp Leu Lys
            35                  40                  45

Trp Trp Tyr Thr Arg
        50

<210> SEQ ID NO 34
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 34

Asn Ser Asp Pro Lys Cys Pro Leu Ser His Glu Gly Tyr Cys Leu Asn
  1               5                  10                  15

Asp Gly Val Cys Met Tyr Ile Gly Thr Leu Asp Arg Tyr Ala Cys Asn
                20                  25                  30

Cys Val Val Gly Tyr Val Gly Glu Arg Cys Gln Tyr Arg Asp Leu Lys
            35                  40                  45

Trp Leu Ala Leu Arg
        50

<210> SEQ ID NO 35
<211> LENGTH: 53
```

```
<212> TYPE: PRT
<213> ORGANISM: Artificial Sequence
<220> FEATURE:
<223> OTHER INFORMATION: Mutant of human  epidermal growth factor

<400> SEQUENCE: 35

Asn Ser Asn Ser Glu Cys Pro Leu Ser His Asp Gly Tyr Cys Leu Asn
 1               5                  10                  15

Asp Gly Val Cys Lys Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Arg
        35                  40                  45

Trp Trp Gly Leu Arg
    50

<210> SEQ ID NO 36
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 36

Asn Ser Tyr Ser Glu Cys Pro Pro Ser Tyr Asp Gly Tyr Cys Leu His
 1               5                  10                  15

Asp Gly Val Cys Arg Tyr Ile Glu Ala Leu Asp Ser Tyr Ala Cys Asn
            20                  25                  30

Cys Val Val Gly Tyr Ala Gly Glu Arg Cys Gln Tyr Arg Asp Leu Arg
        35                  40                  45

Trp Trp Gly Arg Arg
    50

<210> SEQ ID NO 37
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 37

Asn Ser Asn Ser Glu Cys Pro Arg Ser His Asp Gly Tyr Cys Leu Asn
 1               5                  10                  15

Asp Gly Val Cys Met Tyr Ile Glu Ala Leu Asp Arg Tyr Ala Cys Asn
            20                  25                  30

Cys Val Val Gly Tyr Val Gly Glu Arg Cys Gln Tyr Arg Asp Leu Arg
        35                  40                  45

Trp Trp Gly Leu Arg
    50

<210> SEQ ID NO 38
<211> LENGTH: 53
<212> TYPE: PRT
<213> ORGANISM: Artificial Sequence
<220> FEATURE:
<223> OTHER INFORMATION: Mutant of human  epidermal growth factor

<400> SEQUENCE: 38

Ser Ser Gly Ser Glu Cys Pro Leu Ser His Asp Gly Tyr Cys Leu Asn
 1               5                  10                  15

Asp Gly Val Cys Met Tyr Ile Glu Ala Leu Asp Lys Tyr Ala Cys Asn
            20                  25                  30

Cys Val Val Gly Tyr Val Gly Glu Arg Cys Gln Tyr Arg Asp Leu Arg
```

```
                35                  40                  45

Trp Trp Ala Arg Arg
 50
```

<210> SEQ ID NO 39
<211> LENGTH: 53
<212> TYPE: PRT
<213> ORGANISM: Mus musculus

<400> SEQUENCE: 39

```
Asn Ser Tyr Pro Gly Cys Pro Ser Tyr Asp Gly Tyr Cys Leu Asn
 1               5                  10                  15

Gly Gly Val Cys Met His Ile Glu Ser Leu Asp Ser Tyr Thr Cys Asn
                20                  25                  30

Cys Val Ile Gly Tyr Ser Gly Asp Arg Cys Gln Thr Arg Asp Leu Arg
                35                  40                  45

Trp Trp Glu Leu Arg
 50
```

<210> SEQ ID NO 40
<211> LENGTH: 53
<212> TYPE: PRT
<213> ORGANISM: Rattus norvegicus

<400> SEQUENCE: 40

```
Asn Ser Asn Thr Gly Cys Pro Ser Tyr Asp Gly Tyr Cys Leu Asn
 1               5                  10                  15

Gly Gly Val Cys Met Tyr Val Glu Ser Val Asp Arg Tyr Val Cys Asn
                20                  25                  30

Cys Val Ile Gly Tyr Ile Gly Glu Arg Cys Gln His Arg Asp Leu Arg
                35                  40                  45

Trp Trp Lys Leu Arg
 50
```

<210> SEQ ID NO 41
<211> LENGTH: 53
<212> TYPE: PRT
<213> ORGANISM: Sus scrofa

<400> SEQUENCE: 41

```
Asn Ser Tyr Ser Glu Cys Pro Pro Ser His Asp Gly Tyr Cys Leu His
 1               5                  10                  15

Gly Gly Val Cys Met Tyr Ile Glu Ala Val Asp Ser Tyr Ala Cys Asn
                20                  25                  30

Cys Val Phe Gly Tyr Val Gly Glu Arg Cys Gln His Arg Asp Leu Lys
                35                  40                  45

Trp Trp Glu Leu Arg
 50
```

<210> SEQ ID NO 42
<211> LENGTH: 52
<212> TYPE: PRT
<213> ORGANISM: Canis familiaris

<400> SEQUENCE: 42

```
Asn Gly Tyr Arg Glu Cys Pro Ser Tyr Asp Gly Tyr Cys Leu Tyr
 1               5                  10                  15

Asn Gly Val Cys Met Tyr Ile Glu Ala Val Asp Arg Tyr Ala Cys Asn
                20                  25                  30

Cys Val Phe Gly Tyr Val Gly Glu Arg Cys Gln His Arg Asp Leu Lys
```

Trp Glu Leu Arg
    50

<210> SEQ ID NO 43
<211> LENGTH: 52
<212> TYPE: PRT
<213> ORGANISM: Felis catus

<400> SEQUENCE: 43

Asn Ser Tyr Gln Glu Cys Pro Pro Ser Tyr Asp Gly Tyr Cys Leu Tyr
1               5                   10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
        35                  40                  45

Trp Glu Leu Arg
    50

<210> SEQ ID NO 44
<211> LENGTH: 50
<212> TYPE: PRT
<213> ORGANISM: Cavia porcellus

<400> SEQUENCE: 44

Gln Asp Ala Pro Gly Cys Pro Pro Ser His Asp Gly Tyr Cys Leu His
1               5                   10                  15

Gly Gly Val Cys Met His Ile Glu Ser Leu Asn Thr Tyr Ala Cys Asn
            20                  25                  30

Cys Val Ile Gly Tyr Val Gly Glu Arg Cys Glu His Gln Asp Leu Asp
        35                  40                  45

Trp Glu
    50

<210> SEQ ID NO 45
<211> LENGTH: 48
<212> TYPE: PRT
<213> ORGANISM: Equus caballus

<400> SEQUENCE: 45

Asn Ser Tyr Gln Glu Cys Ser Gln Ser Tyr Asp Gly Tyr Cys Leu His
1               5                   10                  15

Gly Gly Lys Cys Val Tyr Leu Val Gln Val Asp Thr His Ala Cys Asn
            20                  25                  30

Cys Val Val Gly Tyr Val Gly Glu Arg Cys Gln His Gln Asp Leu Arg
        35                  40                  45

<210> SEQ ID NO 46
<211> LENGTH: 48
<212> TYPE: PRT
<213> ORGANISM: Oryctolagus cuniculus

<400> SEQUENCE: 46

Ser His Phe Asn Gln Cys Pro Asp Ser His Thr Gln Phe Cys Phe His
1               5                   10                  15

```
Gly Thr Cys Arg Phe Leu Val Gln Glu Asp Lys Pro Ala Cys Val Cys
             20                  25                  30

His Ser Gly Tyr Val Gly Ala Arg Cys Glu His Ala Asp Leu Leu Ala
         35                  40                  45

<210> SEQ ID NO 47
<211> LENGTH: 53
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2, 3, 4,  5, 8, 9, 10, 11, 13, 16, 17, 19, 21, 24,
      25, 26, 28, 30, 32, 34, 35, 38, 45, 46, 48, 49, 50, 51, 52
<223> OTHER INFORMATION: Xaa = any amino acid

<400> SEQUENCE: 47

Xaa Xaa Xaa Xaa Xaa Cys Pro Xaa Xaa Xaa Xaa Gly Xaa Cys Leu Xaa
 1               5                  10                  15

Xaa Gly Xaa Cys Xaa Tyr Ile Xaa Xaa Xaa Asp Xaa Tyr Xaa Cys Xaa
             20                  25                  30

Cys Xaa Xaa Gly Tyr Xaa Gly Glu Arg Cys Gln Tyr Xaa Xaa Leu Xaa
         35                  40                  45

Xaa Xaa Xaa Xaa Arg
     50

<210> SEQ ID NO 48
<211> LENGTH: 6
<212> TYPE: PRT
<213> ORGANISM: Homo sapiens

<400> SEQUENCE: 48

Gly Glu Arg Cys Gln Tyr
 1               5

<210> SEQ ID NO 49
<211> LENGTH: 53
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ser, Lys, Tyr, Thr or His
<220> FEATURE:
<221> NAME/KEY: VARIANT
<222> LOCATION: 2
<223> OTHER INFORMATION: Xaa = Gly or Arg
<220> FEATURE:
<221> NAME/KEY: VARIANT
<222> LOCATION: 3
<223> OTHER INFORMATION: Xaa = Asn, Gly or Tyr
<220> FEATURE:
<221> NAME/KEY: VARIANT
<222> LOCATION: 4
<223> OTHER INFORMATION: Xaa = Pro or Phe
<220> FEATURE:
<221> NAME/KEY: VARIANT
<222> LOCATION: 5
<223> OTHER INFORMATION: Xaa = Gly or Lys
<220> FEATURE:
<221> NAME/KEY: VARIANT
<222> LOCATION: 8
<223> OTHER INFORMATION: Xaa = Pro, Ser or Arg
<220> FEATURE:
<221> NAME/KEY: VARIANT
<222> LOCATION: 9
<223> OTHER INFORMATION: Xaa = Pro
<220> FEATURE:
```

```
<221> NAME/KEY: VARIANT
<222> LOCATION: 10
<223> OTHER INFORMATION: Xaa = Tyr
<220> FEATURE:
<221> NAME/KEY: VARIANT
<222> LOCATION: 11
<223> OTHER INFORMATION: Xaa = Asn, Ser or Glu
<220> FEATURE:
<221> NAME/KEY: VARIANT
<222> LOCATION: 13
<223> OTHER INFORMATION: Xaa = His
<220> FEATURE:
<221> NAME/KEY: VARIANT
<222> LOCATION: 16
<223> OTHER INFORMATION: Xaa = Gln or Asn
<220> FEATURE:
<221> NAME/KEY: VARIANT
<222> LOCATION: 17, 46
<223> OTHER INFORMATION: Xaa = Gly
<220> FEATURE:
<221> NAME/KEY: VARIANT
<222> LOCATION: 19, 34, 35
<223> OTHER INFORMATION: Xaa = Ala
<220> FEATURE:
<221> NAME/KEY: VARIANT
<222> LOCATION: 21
<223> OTHER INFORMATION: Xaa = Val, Arg or Lys
<220> FEATURE:
<221> NAME/KEY: VARIANT
<222> LOCATION: 24
<223> OTHER INFORMATION: Xaa = Lys or Gly
<220> FEATURE:
<221> NAME/KEY: VARIANT
<222> LOCATION: 25
<223> OTHER INFORMATION: Xaa = Thr
<220> FEATURE:
<221> NAME/KEY: VARIANT
<222> LOCATION: 26, 30
<223> OTHER INFORMATION: Xaa = Val
<220> FEATURE:
<221> NAME/KEY: VARIANT
<222> LOCATION: 28
<223> OTHER INFORMATION: Xaa = Arg, Ser or Thr
<220> FEATURE:
<221> NAME/KEY: VARIANT
<222> LOCATION: 32
<223> OTHER INFORMATION: Xaa = Ser
<220> FEATURE:
<221> NAME/KEY: VARIANT
<222> LOCATION: 38
<223> OTHER INFORMATION: Xaa = Thr, Ala, Val, Asn or Leu
<220> FEATURE:
<221> NAME/KEY: VARIANT
<222> LOCATION: 45
<223> OTHER INFORMATION: Xaa = Gly, Gln or Pro
<220> FEATURE:
<221> NAME/KEY: VARIANT
<222> LOCATION: 48
<223> OTHER INFORMATION: Xaa = Arg or Thr
<220> FEATURE:
<221> NAME/KEY: VARIANT
<222> LOCATION: 49
<223> OTHER INFORMATION: Xaa = Arg
<220> FEATURE:
<221> NAME/KEY: VARIANT
<222> LOCATION: 50
<223> OTHER INFORMATION: Xaa = Leu
<220> FEATURE:
<221> NAME/KEY: VARIANT
<222> LOCATION: 51
<223> OTHER INFORMATION: Xaa = Gly, Ala, Trp, Lys or Tyr
<220> FEATURE:
<221> NAME/KEY: VARIANT
<222> LOCATION: 52
<223> OTHER INFORMATION: Xaa = Pro, Arg or Thr
```

```
<400> SEQUENCE: 49

Xaa Xaa Xaa Xaa Xaa Cys Pro Xaa Xaa Xaa Xaa Gly Xaa Cys Leu Xaa
 1               5                  10                      15

Xaa Gly Xaa Cys Xaa Tyr Ile Xaa Xaa Xaa Asp Xaa Tyr Xaa Cys Xaa
             20                  25                  30

Cys Xaa Xaa Gly Tyr Xaa Gly Glu Arg Cys Gln Tyr Xaa Xaa Leu Xaa
         35                  40                  45

Xaa Xaa Xaa Xaa Arg
 50
```